(12) United States Patent
Parham et al.

(10) Patent No.: US 10,991,892 B2
(45) Date of Patent: Apr. 27, 2021

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Christof Pflumm, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 424 days.

(21) Appl. No.: 14/416,879

(22) PCT Filed: Jun. 25, 2013

(86) PCT No.: PCT/EP2013/001861
§ 371 (c)(1),
(2) Date: Jan. 23, 2015

(87) PCT Pub. No.: WO2014/015931
PCT Pub. Date: Jan. 30, 2014

(65) Prior Publication Data
US 2015/0214489 A1 Jul. 30, 2015

(30) Foreign Application Priority Data
Jul. 23, 2012 (EP) .................................... 12005368

(51) Int. Cl.
| | | |
|---|---|---|
| H01L 51/54 | (2006.01) | |
| H01L 51/00 | (2006.01) | |
| C07D 403/10 | (2006.01) | |
| C07D 403/14 | (2006.01) | |
| C07D 405/14 | (2006.01) | |
| C09K 11/02 | (2006.01) | |
| H01L 51/50 | (2006.01) | |

(52) U.S. Cl.
CPC ........ H01L 51/0072 (2013.01); *C07D 403/10* (2013.01); *C07D 403/14* (2013.01); *C07D 405/14* (2013.01); *C09K 11/025* (2013.01); H01L 51/0067 (2013.01); H01L 51/0073 (2013.01); *H01L 51/5072* (2013.01)

(58) Field of Classification Search
CPC .. C07D 209/82; C07D 403/00; C07D 403/10; C07D 403/14; C07D 405/00; C07D 405/10; C07D 405/14; C09K 11/025; H01L 51/0032; H01L 51/005; H01L 51/0052; H01L 51/0062; H01L 51/0067; H01L 51/0071; H01L 51/0072; H01L 51/0073; H01L 51/0074; H01L 51/50; H01L 51/5012; H01L 51/5016; H01L 51/5072
USPC ....... 428/690, 691, 917, 411.4, 336; 427/58, 427/66; 313/500–512; 257/40, 88–104, 257/E51.001–E51.052; 252/301.16–301.35; 544/215, 229, 331, 544/333
See application file for complete search history.

(56) References Cited

U.S. PATENT DOCUMENTS

| | | | |
|---|---|---|---|
| 8,815,418 B2 | 8/2014 | Kim et al. | |
| 8,945,728 B2 | 2/2015 | Ishibashi et al. | |
| 2007/0257600 A1* | 11/2007 | Matsuura | H01L 51/0067 313/498 |
| 2010/0060154 A1* | 3/2010 | Nomura | C07D 263/57 313/504 |
| 2010/0258790 A1* | 10/2010 | Fuchs | H01L 51/0061 257/40 |
| 2011/0095282 A1 | 4/2011 | Pflumm et al. | |
| 2012/0056171 A1 | 3/2012 | Kim et al. | |
| 2012/0223276 A1 | 9/2012 | Parham et al. | |
| 2013/0256645 A1 | 10/2013 | Min et al. | |
| 2014/0034938 A1* | 2/2014 | Ishibashi | C07D 239/26 257/40 |
| 2014/0312338 A1 | 10/2014 | Mizutani et al. | |

FOREIGN PATENT DOCUMENTS

| | | | |
|---|---|---|---|
| CN | 102421868 A | 4/2012 | |
| EP | 02431445 A2 | 3/2012 | |
| JP | 2015006995 A | 1/2015 | |
| KR | 20110016047 A | 2/2011 | |
| KR | 20110058250 A | 6/2011 | |
| KR | 20110066766 A | 6/2011 | |
| KR | 20110130904 A | 12/2011 | |
| KR | 20120029751 A | 3/2012 | |
| KR | 20130113263 A | 10/2013 | |
| WO | WO-2010131930 A2 | 11/2010 | |
| WO | WO-2011055914 A1 | 5/2011 | |
| WO | WO-2011057706 A2 | 5/2011 | |
| WO | WO-2011108901 A2 | 9/2011 | |
| WO | WO-2012/087960 A1 | 6/2012 | |
| WO | WO-2012074210 A2 | 6/2012 | |
| WO | WO-2012137958 A1 * | 10/2012 | ........... C07D 239/26 |
| WO | WO-2013077362 A1 | 5/2013 | |
| WO | WO-20130100540 A1 | 7/2013 | |

OTHER PUBLICATIONS

Chinese office action dated Oct. 19, 2015 for Chinese corresponding application # 201380039254.8.
International Search Report for PCT/EP2013/001861 dated Oct. 14, 2013.
Japanese Office Action Translation for Patent Application No. 2015-523432, dated Mar. 28, 2017.

* cited by examiner

*Primary Examiner* — Andrew K Bohaty
(74) *Attorney, Agent, or Firm* — Faegre Drinker Biddle & Reath LLP

(57) ABSTRACT

The present invention relates to carbazole derivatives, in particular for use as triplet matrix materials in organic electroluminescent devices. The invention further relates to a method for producing the compounds according to the invention and to electronic devices comprising same.

9 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2013/001861, filed Jun. 25, 2013, which claims benefit of European Application No. 12005368.1, filed Jul. 23, 2012, both of which are incorporated herein by reference in their entirety.

The present invention describes carbazole derivatives, in particular for use as triplet matrix materials in organic electroluminescent devices. The invention furthermore relates to a process for the preparation of the compounds according to the invention and to electronic devices comprising these compounds.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed are frequently organometallic complexes which exhibit phosphorescence instead of fluorescence. For quantum-mechanical reasons, an up to four-fold energy and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit triplet emission (phosphorescence).

The properties of phosphorescent OLEDs are not determined only by the triplet emitters employed. In particular, the other materials used, such as, for example, matrix materials, are also of particular importance here. Improvements in these materials may thus also result in significant improvements in the OLED properties.

In accordance with the prior art, the matrix materials used for phosphorescent emitters are, inter alia, indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic compounds, such as triazine. The matrix materials used for phosphorescent emitters are furthermore, for example, bisdibenzofuran derivatives (for example in accordance with EP 2301926). However, there is still a need for improvement on use of these matrix materials, in particular with respect to the efficiency, the lifetime and the operating voltage of the device.

The object of the present invention is the provision of compounds which are suitable for use in a fluorescent or in particular in a phosphorescent OLED, in particular as matrix material. In particular, the object of the present invention is to provide matrix materials which are also suitable for green- and possibly also for blue-phosphorescent OLEDs and which result in good efficiency, a long lifetime and a low operating voltage. The properties of the matrix materials in particular also have a significant influence on the lifetime and the efficiency of the organic electroluminescent device.

WO 2011/057706 discloses carbazole derivatives which are substituted by two triphenyltriazine groups. Further improvements are still desirable here, in particular with respect to the triplet level and to the sublimation stability.

WO 2011/055914 discloses a carbazole derivative which is substituted by a triphenyltriazine group, where one of the phenyl groups is substituted by a dimesitylboranyl group. The characterising feature of this compound is the presence of the diarylboranyl group. Compounds without these substituents are not disclosed.

WO 2011/149240 discloses a triphenylene derivative which is substituted by a carbazole group and a diphenyltriazine group. The characteristic feature of this compound is the presence of the triphenylene group. Compounds which do not contain a triphenylene are not disclosed.

WO 2011/046182 discloses carbazole-arylene-triazine derivatives which are substituted on the triazine by a fluorenyl group. The characteristic feature of these compounds is the presence of the fluorenyl group. Compounds which do not contain a fluorenyl group as substituent are not disclosed.

In general, further improvements are still desirable in the case of all these compounds.

Surprisingly, it has been found that electroluminescent devices which comprise compounds of the following formula (1) have improvements over the prior art, in particular on use as matrix material for phosphorescent dopants.

The present invention therefore relates to a compound of the following formula (1),

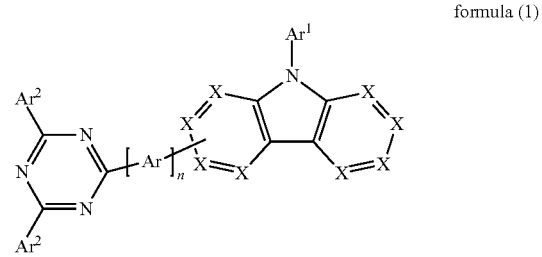

formula (1)

where the following applies to the symbols and indices used:

X is on each occurrence, identically or differently, $CR^1$ or N; or X is C if the group Ar is bonded at this position;

Ar is on each occurrence, identically or differently, a phenylene group, which may be substituted by one or more radicals R, or a fluorenylene or spirobifluorenylene group, which may be substituted by one or more radicals $R^1$;

$Ar^1$ is an aromatic ring system having 6 to 24 aromatic ring atoms which contains no condensed aryl groups having more than 10 aromatic ring atoms and which may be substituted by one or more radicals $R^1$, or is a dibenzofuran or dibenzothiophene group, each of which may be substituted by one or more radicals $R^1$;

$Ar^2$ is on each occurrence, identically or differently, an aryl group, a biaryl group, a triaryl group or quateraryl group, where each individual aryl group in the above-mentioned groups has 6 to 10 aromatic ring atoms and may be substituted by one or more radicals $R^1$, or is a dibenzofuran or dibenzothiophene group, each of which may be substituted by one or more radicals $R^1$;

R is on each occurrence, identically or differently, H, D, F, CN, an aryl group, a biaryl group, a triaryl group or quateraryl group, where each individual aryl group in the above-mentioned groups has 6 to 10 aromatic ring atoms and may be substituted by one or more radicals $R^1$, or a carbazole group which is linked via a carbon atom and which may also be substituted by one or more radicals $R^1$;

$R^1$ is on each occurrence, identically or differently, H, D, F, CN, a straight-chain alkyl or alkoxy group having 1 to 20 C atoms or a branched or cyclic alkyl or alkoxy group having 3 to 20 C atoms, where one or more non-adjacent CH₂ groups may be replaced by R²C=CR², C≡C or O and where one or more H atoms may be replaced by D or F, or an aryl group having 6 to 10 C atoms, which may be substituted by one or more radicals R², or is a dibenzofuran or dibenzothiophene group, each of which may be substituted by one or more radicals R², or a carbazole group which is linked via a carbon atom and which may also be substituted by one or more radicals R², or an aralkyl group having 6 to 10 aromatic ring atoms, which may be substituted by one or more radicals R²; two adjacent substituents R¹ here, together with the atoms to which they are bonded, may also form a mono- or polycyclic, aliphatic ring system with one another;

R² is on each occurrence, identically or differently, H, D or an aliphatic hydrocarbon radical having 1 to 20 C atoms or an aryl group having 6 to 10 ring atoms;

n is 1, 2, 3 or 4, preferably 1, 2 or 3.

Adjacent substituents in the sense of the present invention are substituents which are bonded to carbon atoms which are linked directly to one another. By contrast, substituents which are bonded to different aryl groups are not adjacent substituents in the sense of the present invention.

The aryl group having 6 to 10 aromatic ring atoms, as defined for Ar², R and R¹, is benzene or naphthalene, preferably benzene. The aromatic ring system, as defined for Ar¹, furthermore preferably contains absolutely no condensed aryl groups.

A biaryl group in the sense of the present invention is taken to mean two aryl groups linked directly to one another, for example biphenyl, A triaryl group in the sense of the present invention is taken to mean three aryl groups linked directly to one another, for example terphenyl. A quateraryl group in the sense of the present invention is taken to mean four aryl groups linked directly to one another, for example quaterphenyl. These four aryl groups may be linked to one another in a linear or branched manner.

A condensed aryl group in the sense of the present invention is a group in which two or more aromatic groups are condensed, i.e. annellated, onto one another via a common edge, such as, for example, in naphthalene. By contrast, for example, fluorene is not a condensed aryl group in the sense of the present invention, since the two aromatic groups in fluorene do not have a common edge.

An aromatic ring system in the sense of this invention contains 6 to 24 C atoms in the ring system. An aromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than hydrogen), such, as, for example, a C atom. Thus, for example, systems such as fluorene, 9,9'-spirobifluorene, 9,9-diarylfluorene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, terphenyl or quaterphenyl, are referred to as an aromatic ring system in the sense of this application.

For the purposes of the present invention, an aliphatic hydrocarbon radical or an alkyl group or an alkenyl group, which may contain 1 to 20 C atoms and in which, in addition, individual H atoms or CH₂ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. In general, alkyl, alkenyl, alkynyl, alkoxy or thioalkyl groups in accordance with the present invention may be straight-chain, branched or cyclic, where one or more non-adjacent CH₂ groups may be replaced by the above-mentioned groups; furthermore, one or more H atoms may also be replaced by D or F.

In a preferred embodiment of the invention, a maximum of one group X per ring stands for N and the remaining groups X stand, identically or differently on each occurrence, for CR¹. X particularly preferably stands, identically or differently on each occurrence, for CR¹. Preferred compounds of the formula (1) are therefore the compounds of the following formula (2),

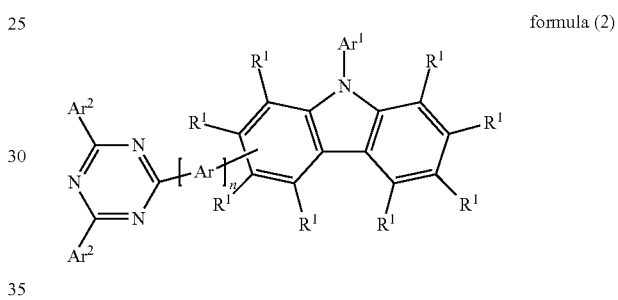

formula (2)

where the symbols and indices used have the meanings given above and the radical R¹ is not present if the group Ar is bonded at this position.

The group Ar may be bonded in the 1-, 2-, 3- or 4-position of the carbazole. In a preferred embodiment of the present invention, the group Ar is bonded in the 1-, 2- or 3-position of the carbazole. Preference is therefore given to the compounds of the following formulae (2a), (2b) and (2c),

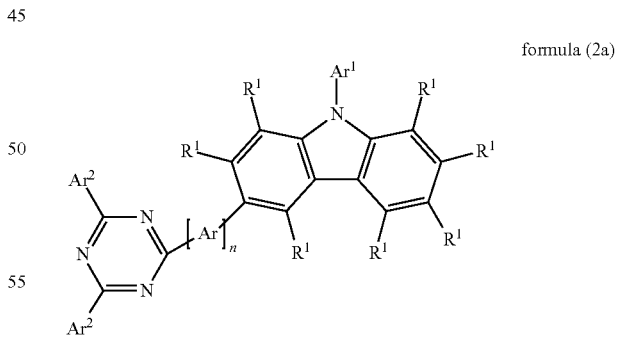

formula (2a)

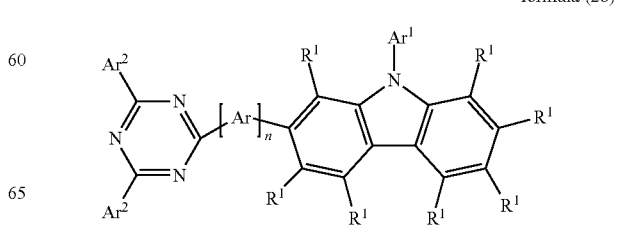

formula (2b)

formula (2c)

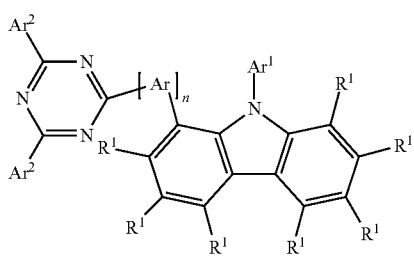

where the symbols and indices used have the meanings given above.

Particular preference is given to the compounds of the above-mentioned formulae (2a) and (2b).

In a preferred embodiment of the invention, n=1, 2 or 3 and Ar stands for a phenylene group, which may be substituted by one or more radicals R. Ar here stands, identically or differently on each occurrence, for a group selected from the following formulae (3), (4) or (5), formula (3)

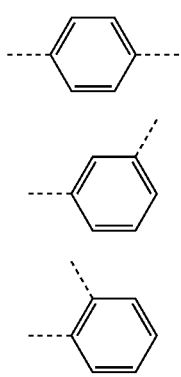

formula (4)

formula (5)

where the dashed bond in each case indicates the linking of these groups and each of these groups may be substituted by one or more radicals R.

In a further preferred embodiment of the invention, n=1 and Ar stands for a fluorenylene or spirobifluorenylene group, which may be substituted by one or more radicals $R^1$.

The group —(Ar)$_n$— particularly preferably stands for a group selected from the formulae (6) to (20), formula (6)

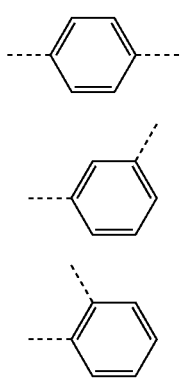

formula (7)

formula (8)

formula (9)

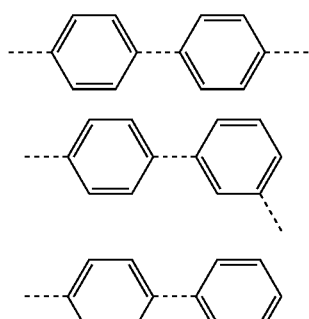

formula (10)

formula (11)

formula (12)

formula (13)

formula (14)

formula (15)

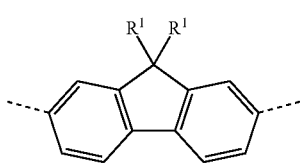

formula (16)

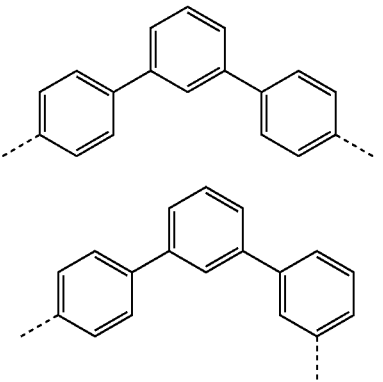

formula (17)

formula (18)

formula (19)

formula (20)

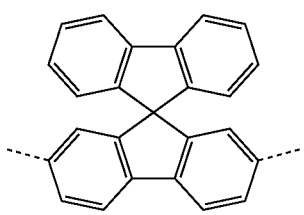

where the dashed bond in each case indicates the linking of these groups, each of these groups may also be substituted by one or more radicals R, and R and $R^1$ have the meanings given above.

The radical R which is bonded to Ar or to the preferred embodiments of Ar described above is preferably selected here, identically or differently on each occurrence, from the group consisting of H, D, F, CN, phenyl, biphenyl or terphenyl, where each of the aryl groups in the above-mentioned groups may be substituted by one or more radicals $R^1$, and $R^1$ preferably stands, identically or differently on each occurrence, for H or an alkyl group having 1 to 5 C atoms, or a carbazole group which is linked via a carbon atom and which may also be substituted by one or more radicals $R^1$. R is particularly preferably selected from the group consisting of H, phenyl, biphenyl or terphenyl or an N-phenylcarbazole group which is linked via a carbon atom.

In a furthermore preferred embodiment of the invention, $Ar^1$ is selected from the group consisting of phenyl, biphenyl, terphenyl or quaterphenyl, each of which may be substituted by one or more radicals $R^1$.

In still a further preferred embodiment of the invention, $Ar^2$ is selected, identically or differently on each occurrence, from the group consisting of phenyl, biphenyl, terphenyl or quaterphenyl, each of which may be substituted by one or more radicals $R^1$.

In still a further preferred embodiment of the invention, $R^1$ is selected on each occurrence, identically or differently, from the group consisting of H, F, a straight-chain alkyl group having 1 to 10 C atoms or a branched or cyclic alkyl group having 3 to 10 C atoms, where one or more non-adjacent $CH_2$ groups may be replaced by $R^2C=CR^2$ and where one or more H atoms may be replaced by F, or an aryl group having 6 to 10 C atoms, which may be substituted by one or more radicals $R^2$, or is a dibenzofuran or dibenzothiophene group, each of which may be substituted by one or more radicals $R^2$, or a carbazole group which is linked via a carbon atom and which may also be substituted by one or more radicals $R^2$.

$R^1$ is particularly preferably selected on each occurrence, identically or differently, from the group consisting of H, a straight-chain alkyl group having 1 to 5 C atoms or a branched or cyclic alkyl group having 3 to 5 C atoms, or an aryl group having 6 to 10 C atoms, which may be substituted by one or more radicals $R^2$.

The above-mentioned embodiments of the invention can be combined with one another as desired. The embodiments mentioned as preferred above are particularly preferably combined with one another.

In a preferred embodiment of the invention, the following thus applies to the symbols and indices used for the compounds of the formula (1), (2), (2a), (2b) and (2c):
Ar stands, identically or differently on each occurrence, for a group of the above-mentioned formula (3), (4) or (5), where n=1, 2 or 3; or stands for a fluorenylene or spirobifluorenylene group, which may be substituted by one or more radicals $R^1$, where n=1;
R is selected, identically or differently on each occurrence, from the group consisting of H, D, F, CN, phenyl, biphenyl or terphenyl, where each of the aryl groups in the above-mentioned groups may be substituted by one or more radicals $R^1$, and $R^1$ preferably stands, identically or differently on each occurrence, for H or an alkyl group having 1 to 5 C atoms, or a carbazole group which is linked via a carbon atom and which may also be substituted by one or more radicals $R^1$.
$Ar^1$ is selected from the group consisting of phenyl, biphenyl, terphenyl or quaterphenyl, each of which may be substituted by one or more radicals $R^1$;
$Ar^2$ is selected, identically or differently on each occurrence, from the group consisting of phenyl, biphenyl, terphenyl or quaterphenyl, each of which may be substituted by one or more radicals $R^1$;
$R^1$ is selected on each occurrence, identically or differently, from the group consisting of H, D, F, a straight-chain alkyl group having 1 to 10 C atoms or a branched or cyclic alkyl group having 3 to 10 C atoms, where one or more non-adjacent $CH_2$ groups may be replaced by $R^2C=CR^2$ and where one or more H atoms may be replaced by F, or an aryl group having 6 to 10 C atoms, which may be substituted by one or more radicals $R^2$, or is a dibenzofuran or dibenzothiophene group, each of which may be substituted by one or more radicals $R^2$; or a carbazole group which is linked via a carbon atom and which may also be substituted by one or more radicals $R^2$.

In a particularly preferred embodiment of the invention, the following thus applies to the symbols and indices used for the compounds of the formula (1), (2), (2a), (2b) and (2c):
—$(Ar)_n$— stands for a group of one of the formulae (6) to (20) shown above;
R is selected, identically or differently on each occurrence, from the group consisting of H, phenyl, biphenyl, terphenyl or an N-phenylcarbazole group which is linked via a carbon atom;
$Ar^1$ is selected from the group consisting of phenyl, biphenyl, terphenyl or quaterphenyl, each of which may be substituted by one or more radicals $R^1$;
$Ar^2$ is selected, identically or differently on each occurrence, from the group consisting of phenyl, biphenyl, terphenyl or quaterphenyl, each of which may be substituted by one or more radicals $R^1$;
$R^1$ is selected on each occurrence, identically or differently, from the group consisting of H, a straight-chain alkyl group having 1 to 5 C atoms or a branched or cyclic alkyl group having 3 to 5 C atoms, or an aryl group having 6 to 10 C atoms, which may be substituted by one or more radicals $R^2$.

Examples of compounds according to the invention are the structures shown below.

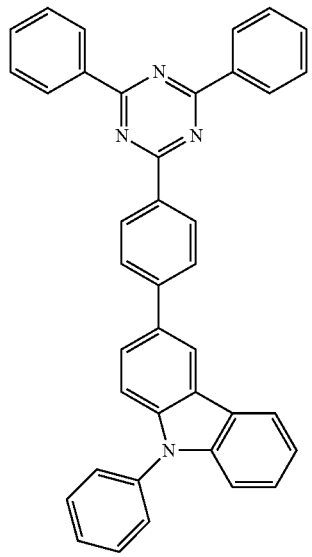

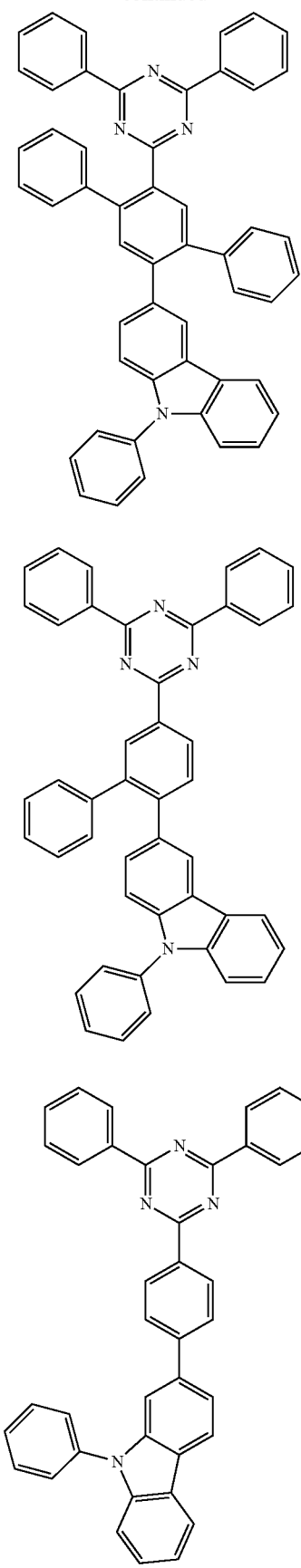
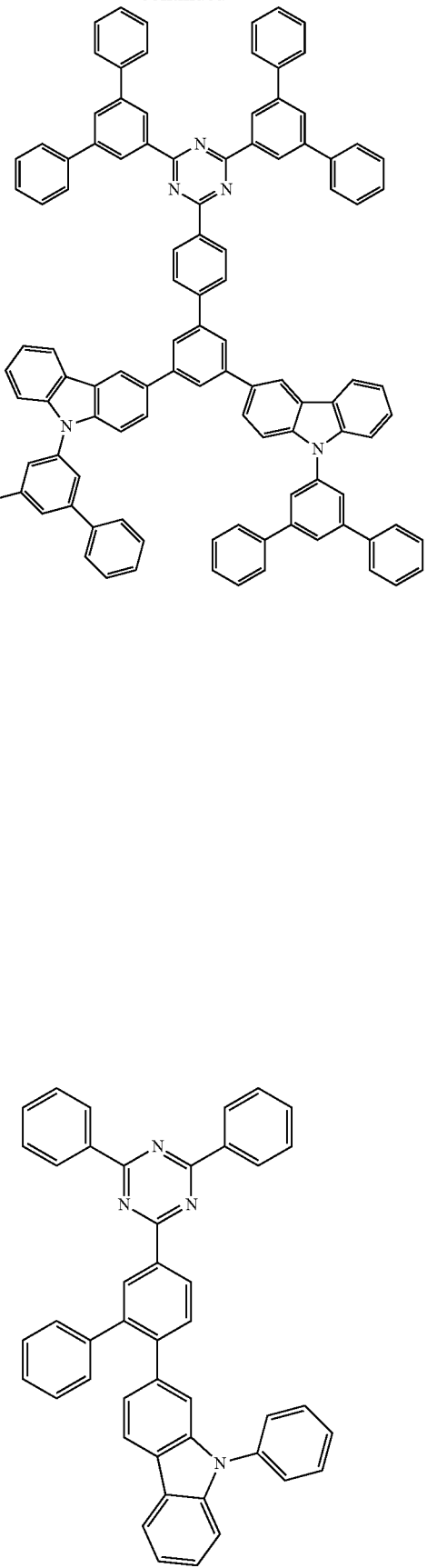

11
-continued
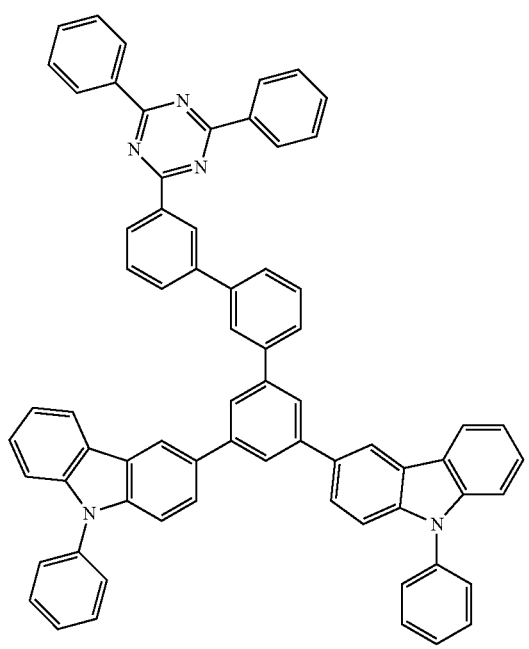
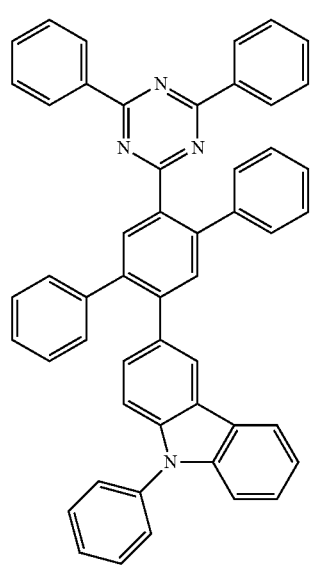
12
-continued
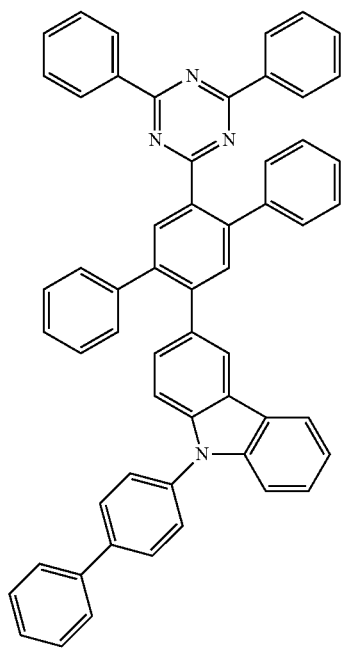
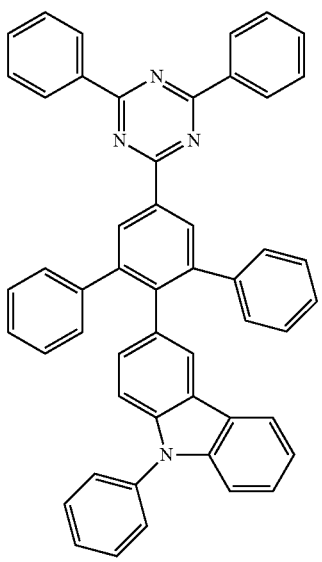

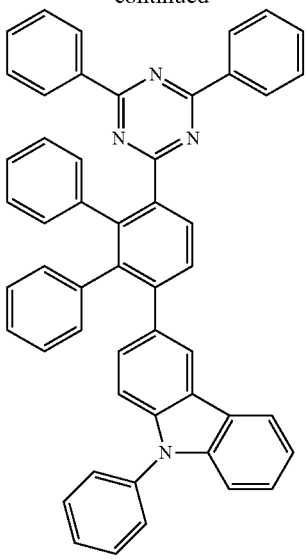
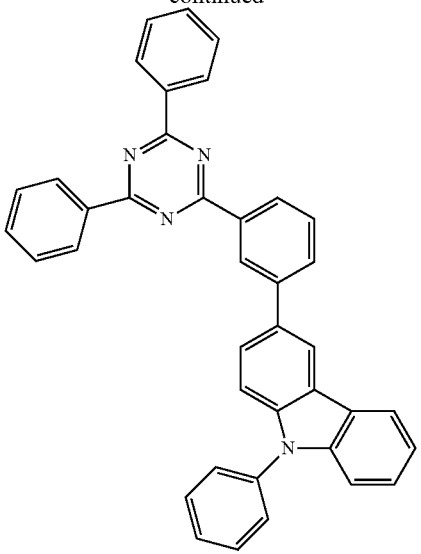
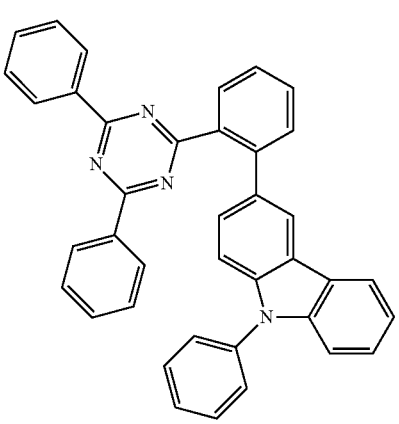
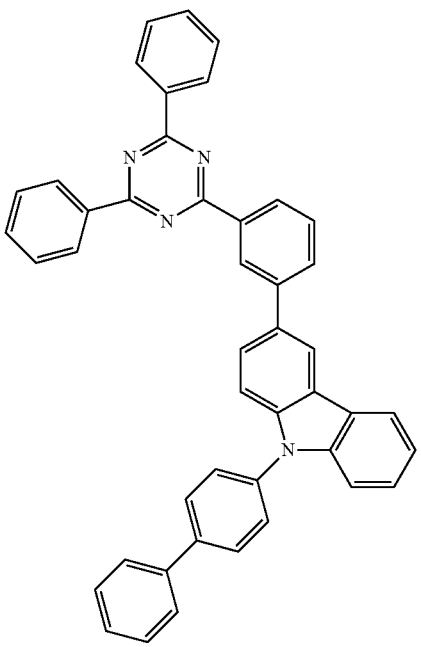

15
-continued
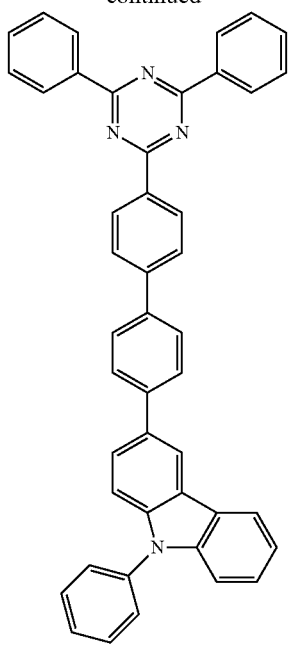
16
-continued
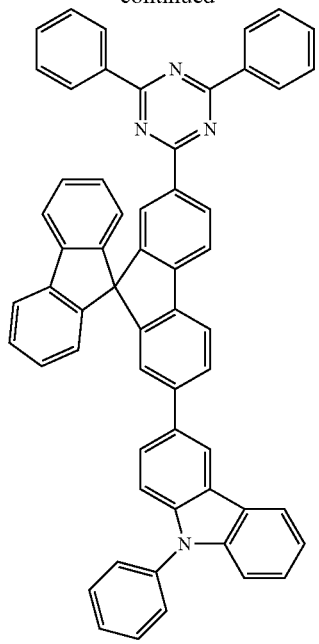
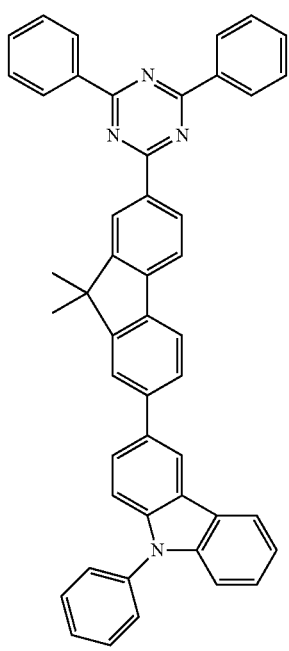
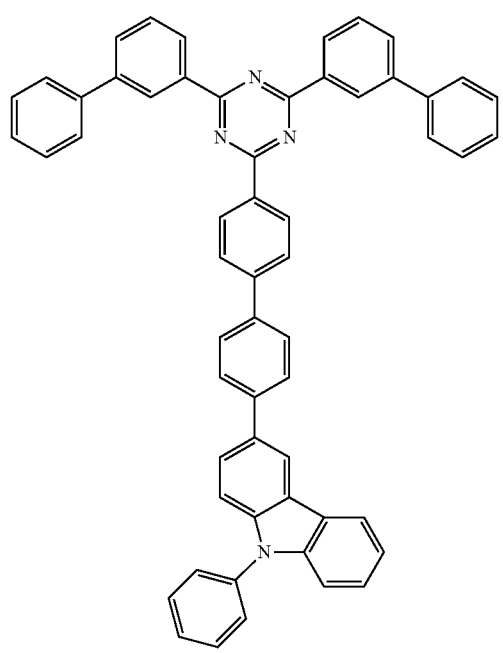

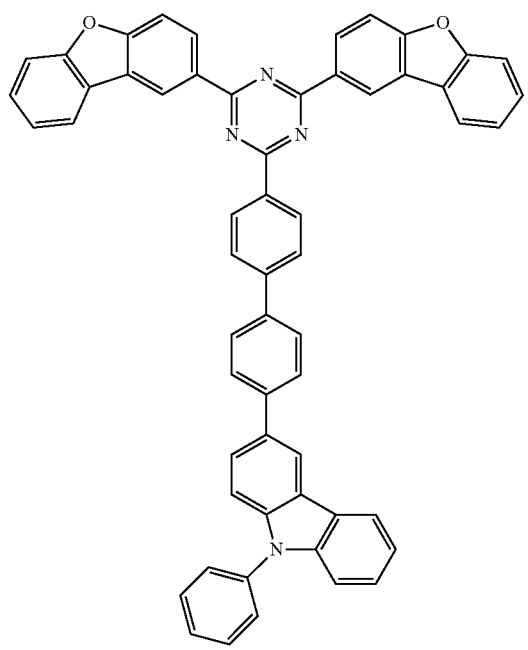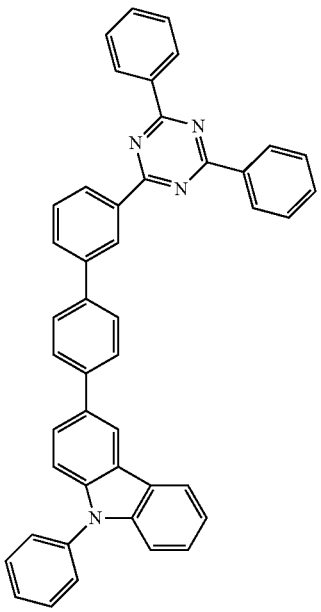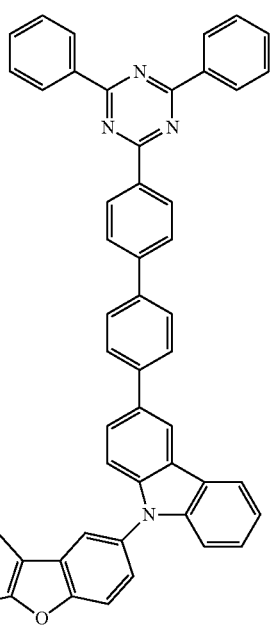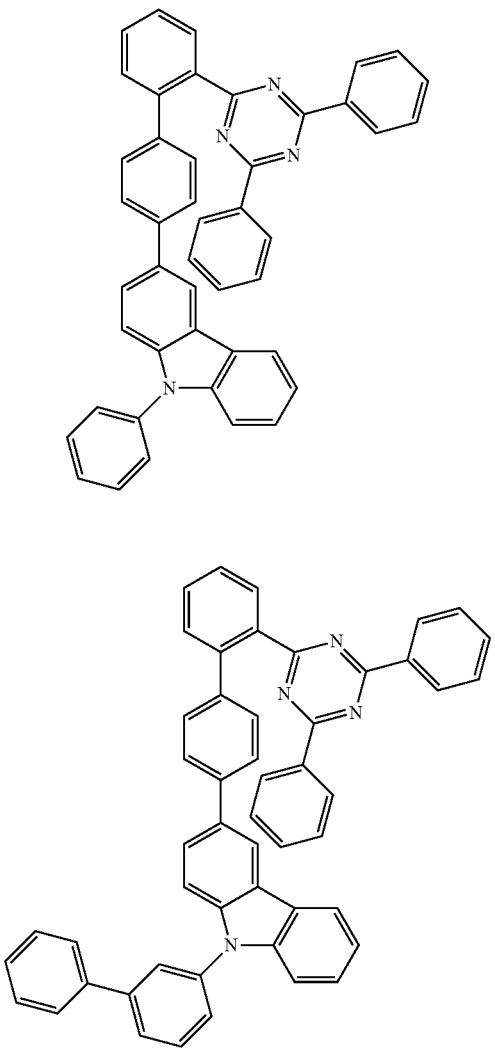

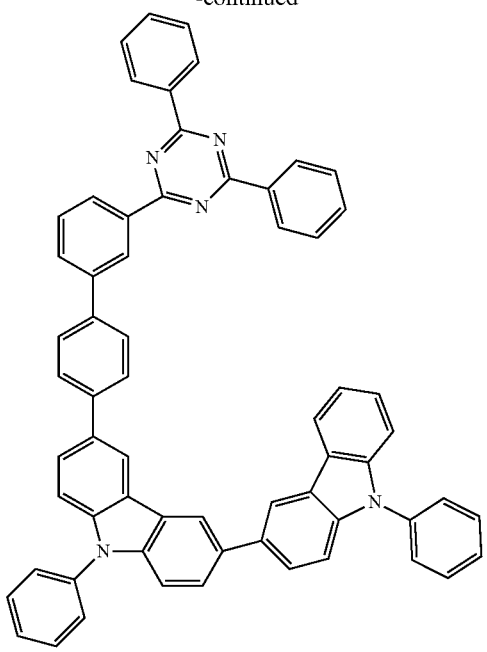
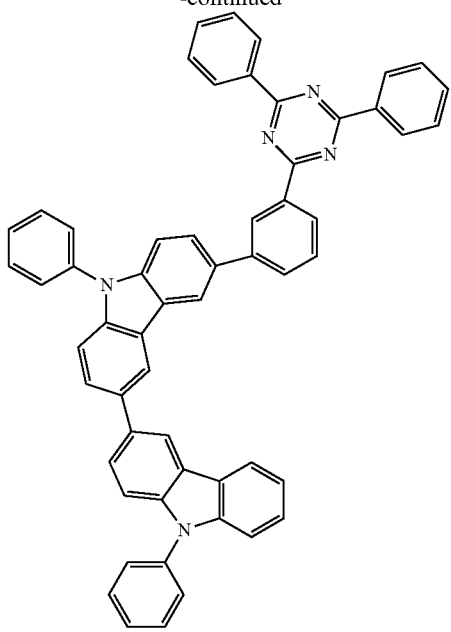
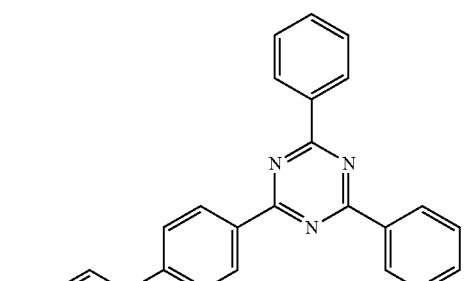
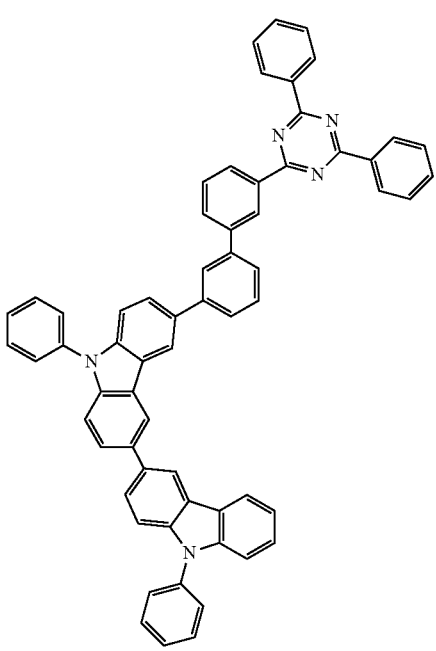
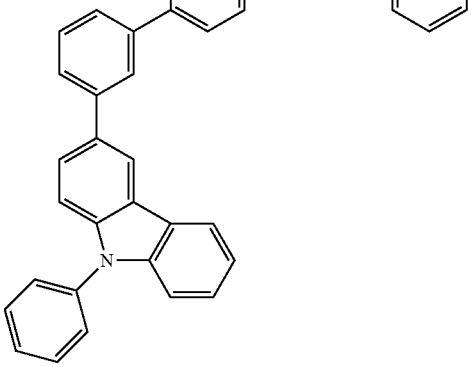
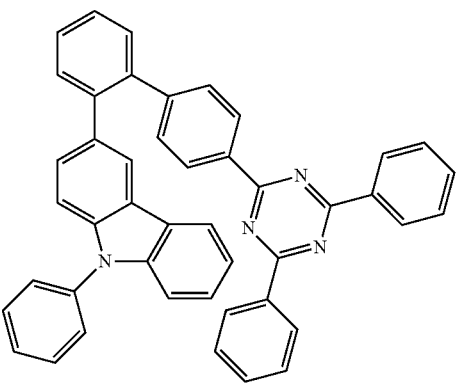

-continued
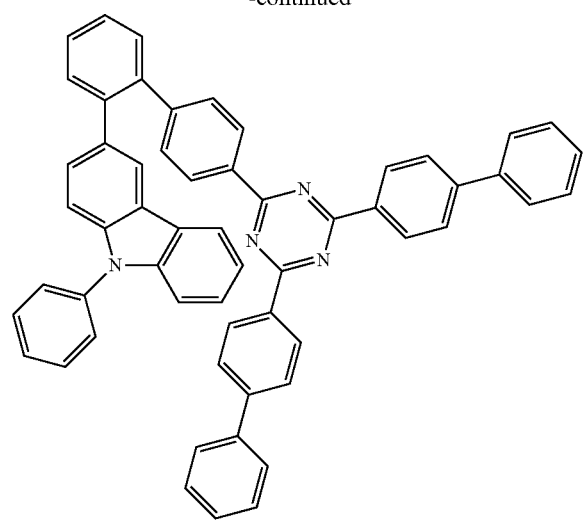
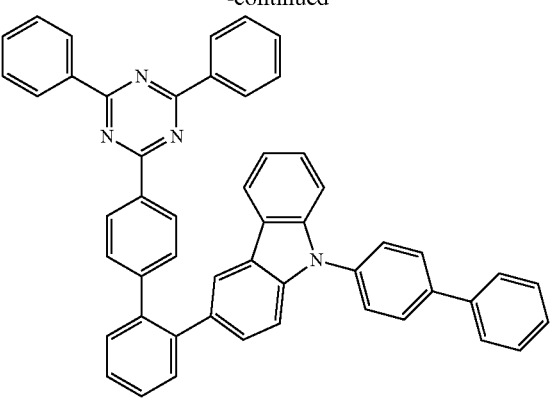
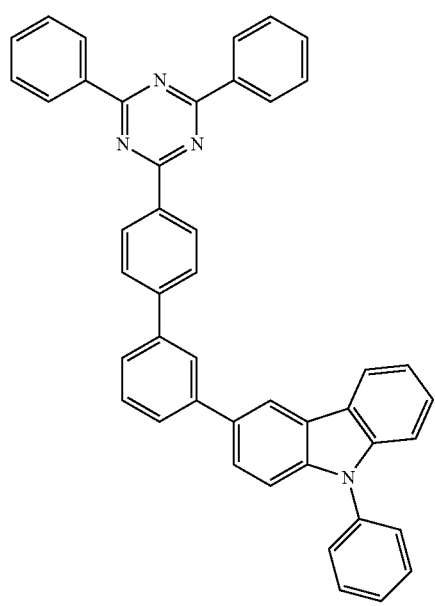
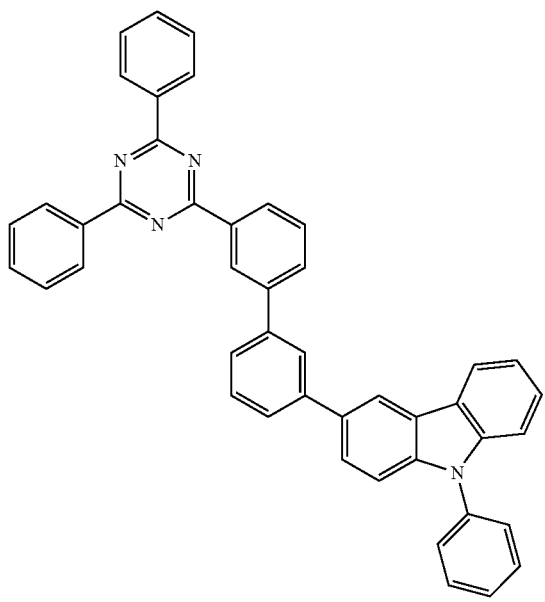
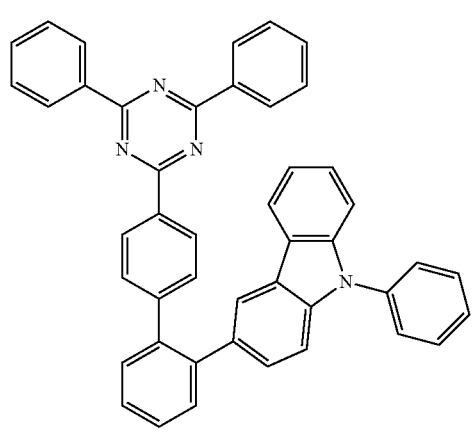
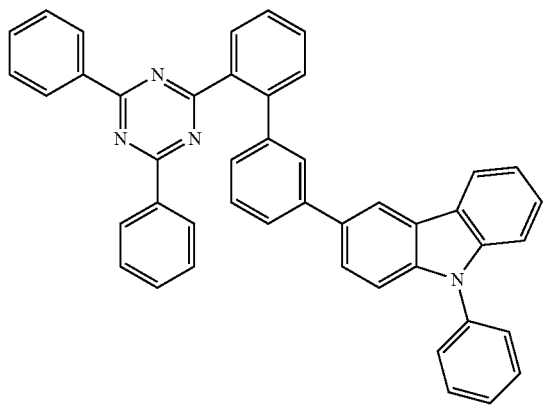

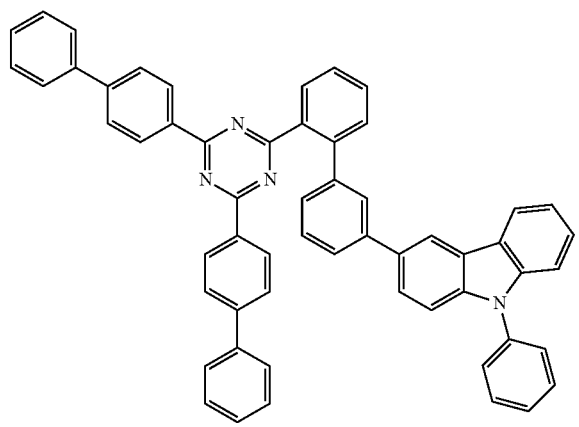
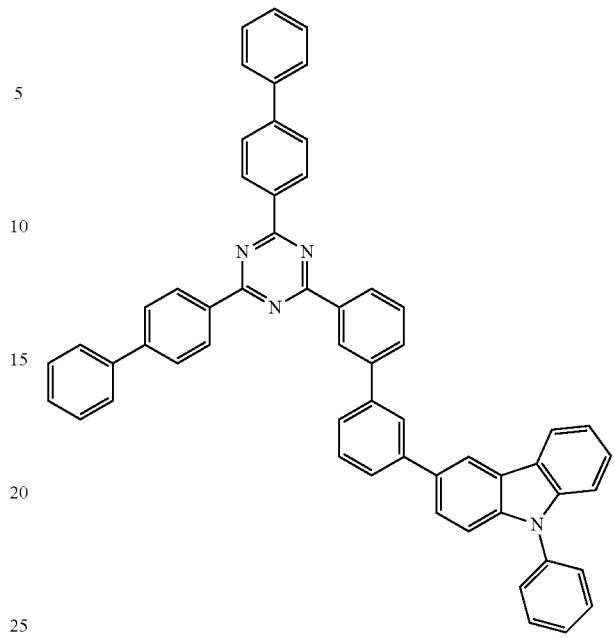
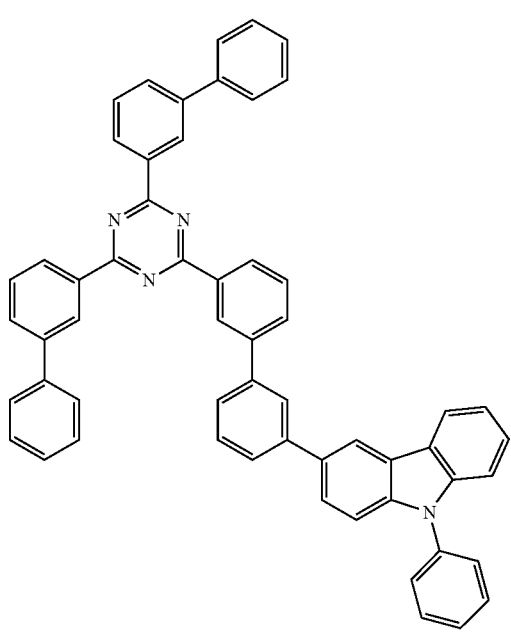
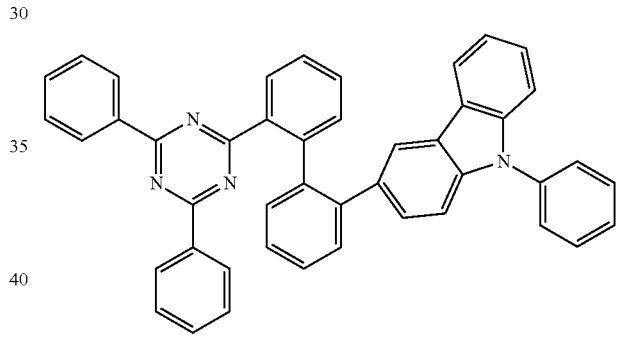
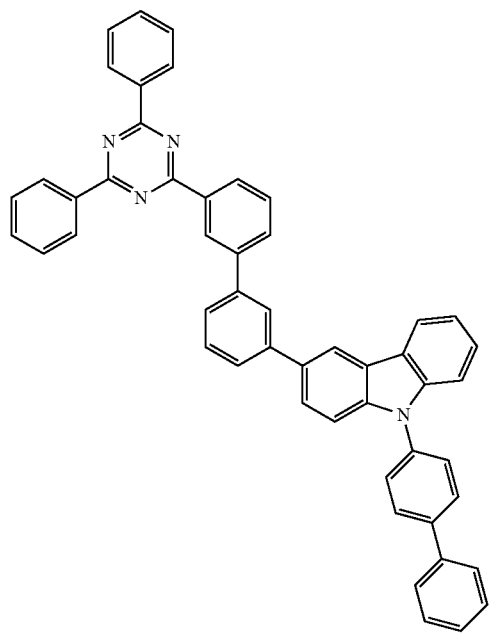
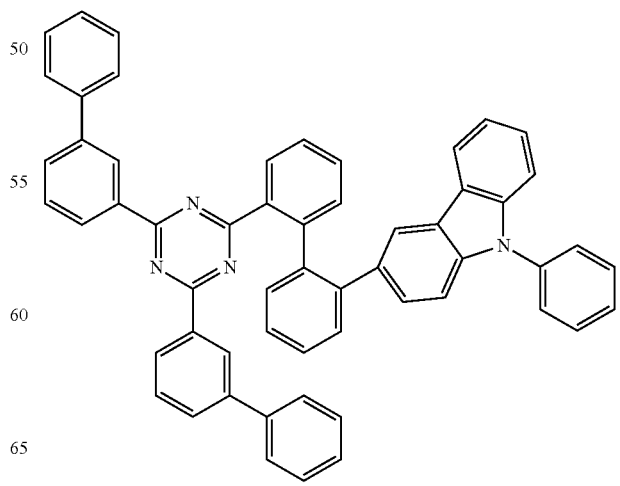

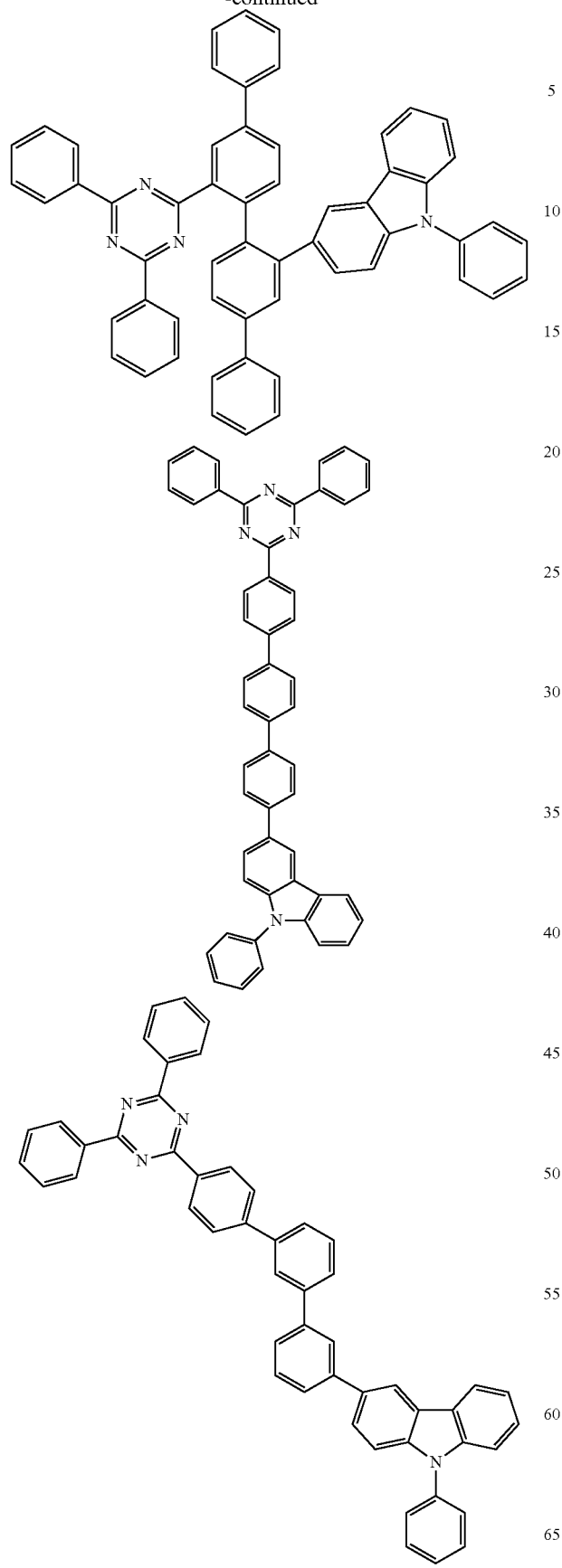

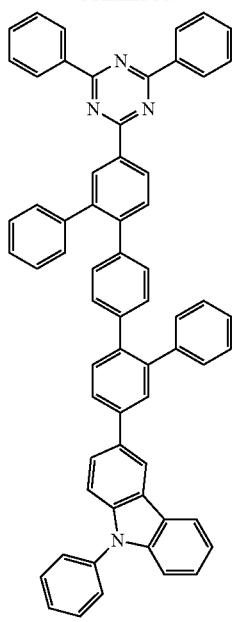
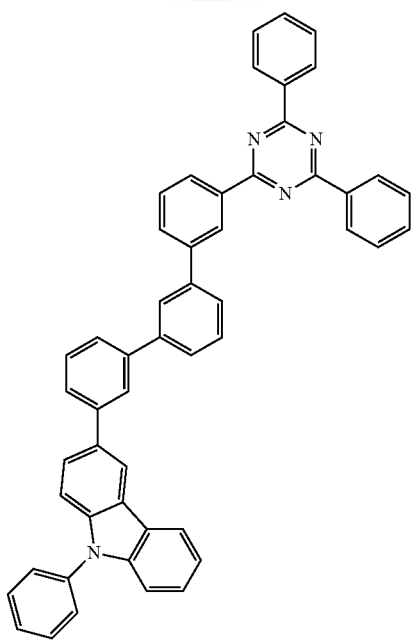
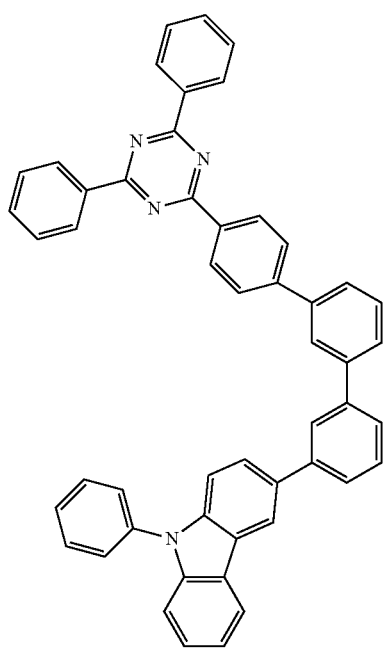
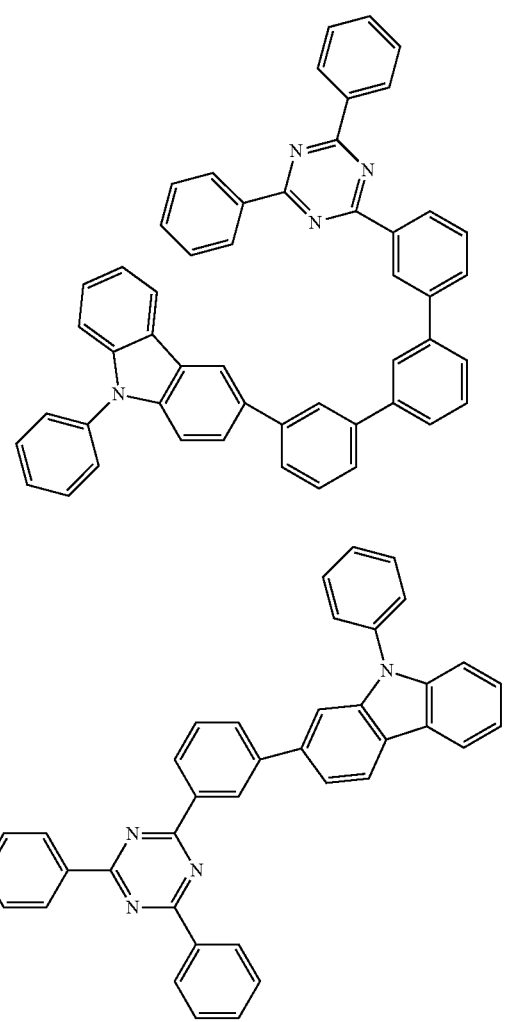

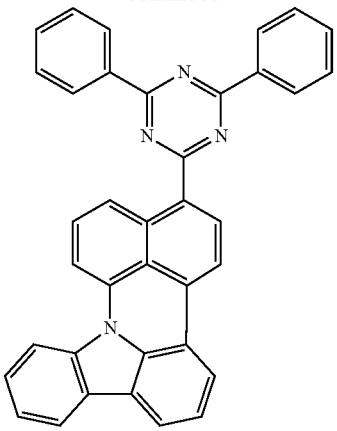
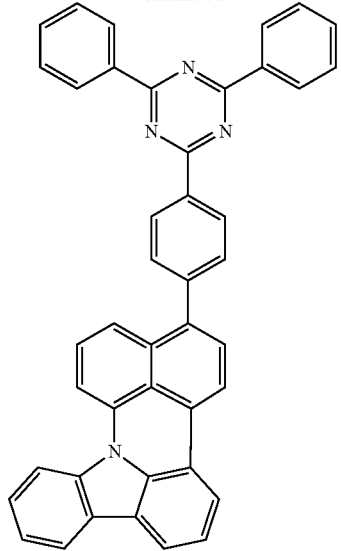
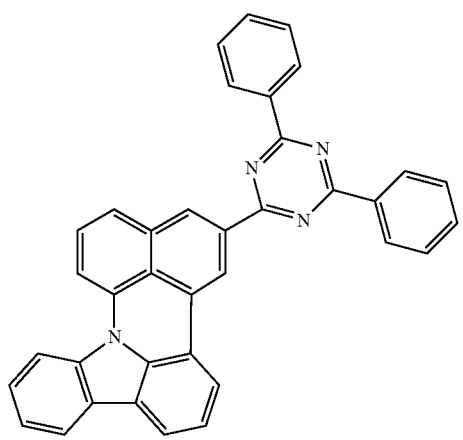
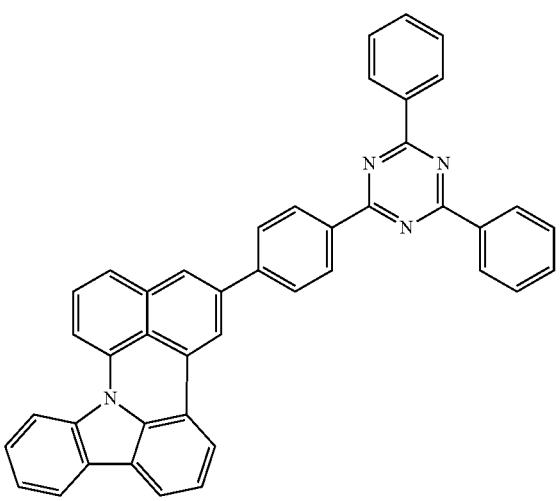
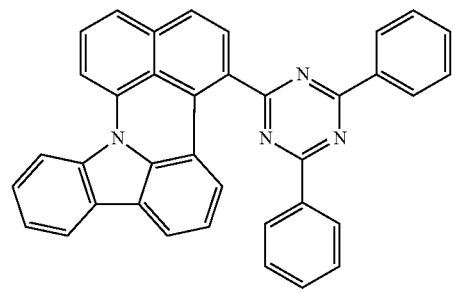
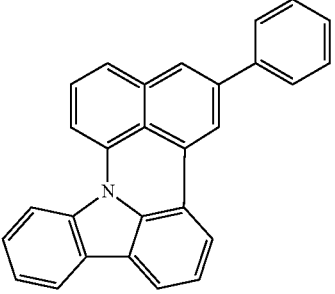

31
-continued
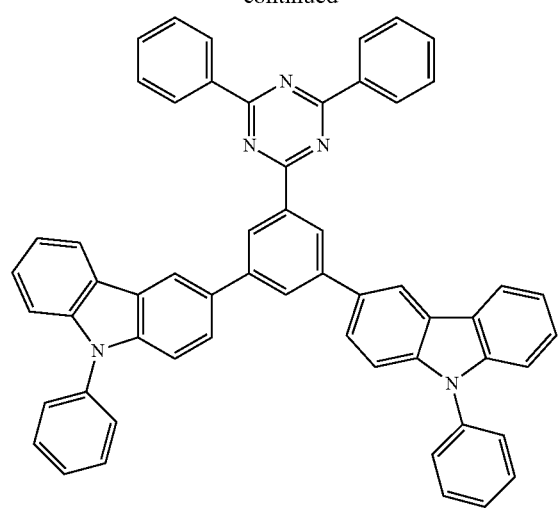
32
-continued
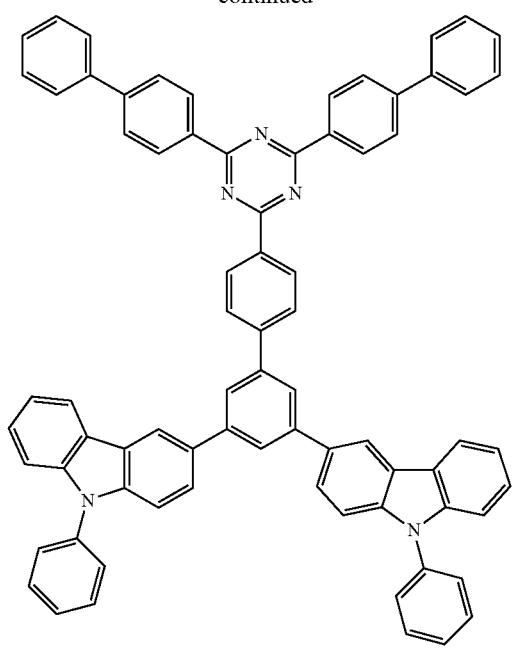
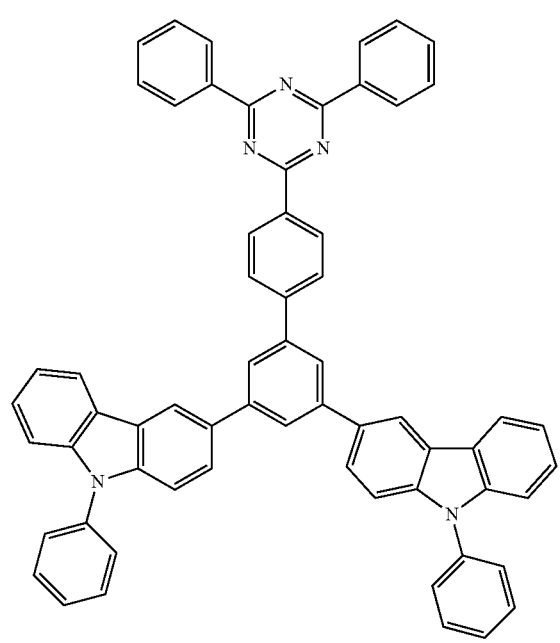
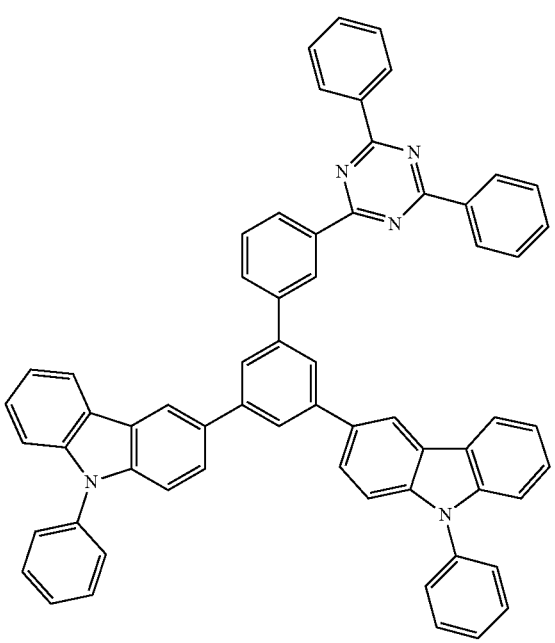

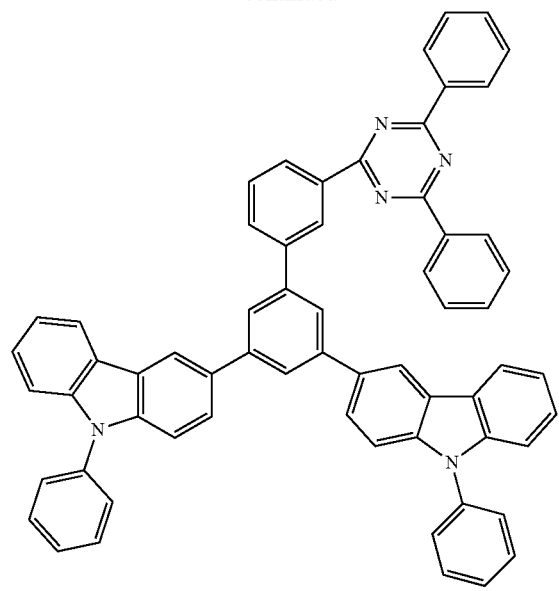
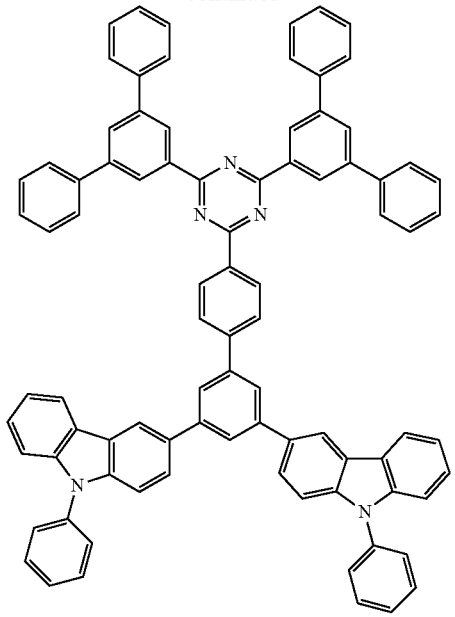
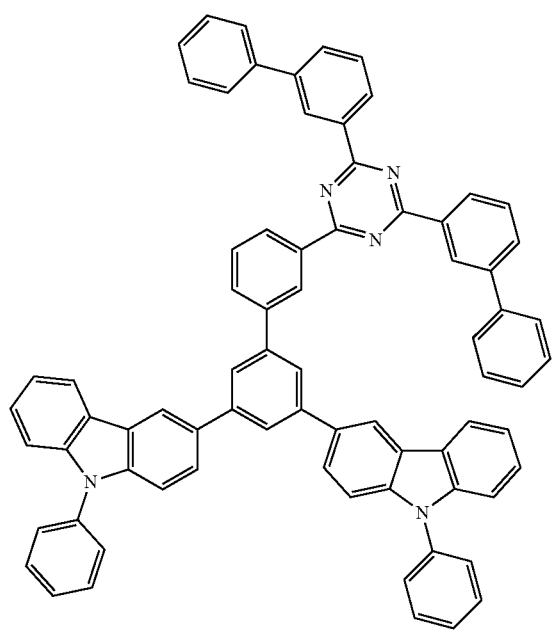
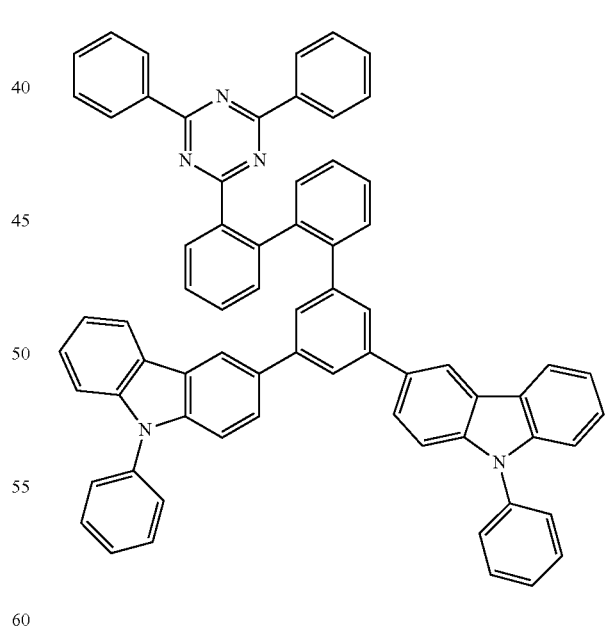
The compounds according to the invention can be prepared by synthetic steps known to the person skilled in the art, such as, for example, bromination, Suzuki coupling, Ullmann coupling, Hartwig-Buchwald coupling, etc. A suitable synthetic process is depicted in general terms in the following Scheme 1:

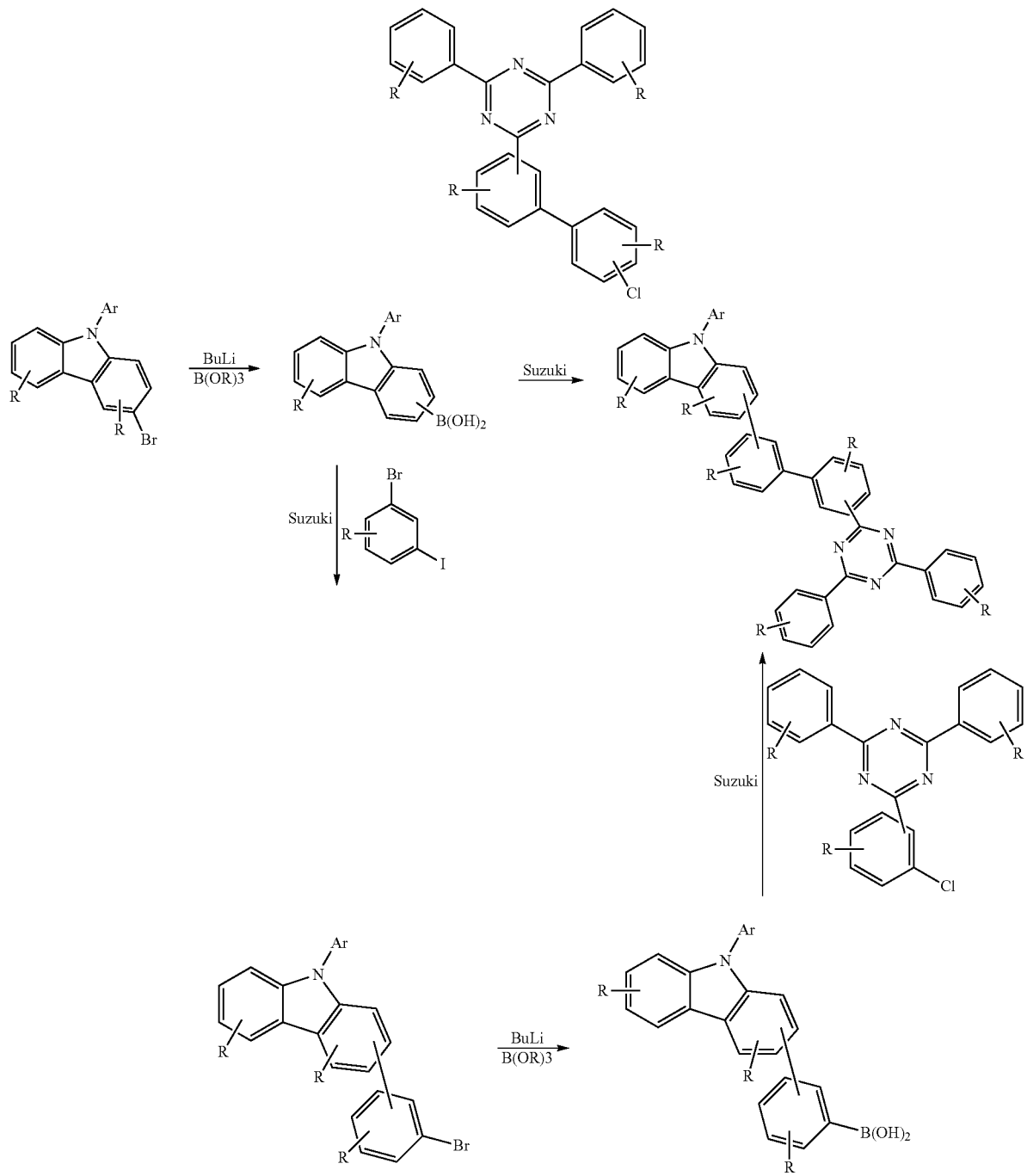

Scheme 1

The invention therefore furthermore relates to a process for the preparation of a compound according to the invention, characterised in that the unit (Ar²)₂triazine-(Ar)ₙ is introduced by a Suzuki coupling.

The present invention furthermore relates to mixtures comprising at least one compound according to the invention and at least one further compound. The further compound can be, for example, a fluorescent or phosphorescent dopant if the compound according to the invention is used as matrix material, in particular a phosphorescent dopant. Suitable dopants are shown below in connection with the organic electroluminescent devices and are also preferred for the mixtures according to the invention.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, a suspension or a mini-emulsion, comprising at least one compound or mixture according to the invention and one or more solvents, in particular organic solvents. The way in which solutions of this type can be prepared is known to the person skilled in the art and described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339 or WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-transport layer or in a hole-injection layer or in an exciton- or electron-blocking layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or in accordance with the preferred embodiments.

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

On use in organic electroluminescent devices, the compounds according to the invention have one or more of the following surprising advantages over the prior art:
1. The power efficiency of corresponding devices is increased compared with systems in accordance with the prior art.
2. The stability of corresponding devices is increased compared with systems in accordance with the prior art, which is evident, in particular, from a longer lifetime.
3. The organic electroluminescent devices according to the invention have a reduced operating voltage.
4. The compounds according to the invention are readily accessible synthetically and in high yield.
5. The compounds according to the invention have very good thermal stability and thus high sublimation stability.

The invention is now explained in greater detail by the following examples, without wishing to restrict it thereby.

EXAMPLES

The following syntheses are carried out, unless indicated otherwise, in dried solvents under a protective-gas atmosphere. The solvents and reagents can be purchased, for example, from Sigma-ALDRICH or ABCR. The corresponding CAS numbers are also given for each of the compounds known from the literature.

Example 1

2,4-Bis-(4-tert-butylphenyl)-6-chloro-1,3,5-triazine

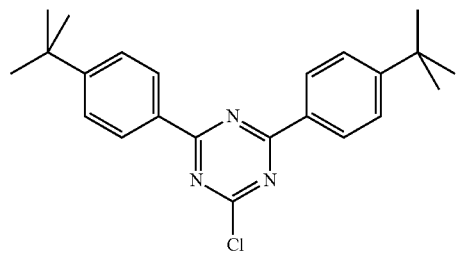 [SMILES: CC(C)(C)c1ccc(-c2nc(Cl)nc(-c3ccc(C(C)(C)C)cc3)n2)cc1]

5.7 g of magnesium (234.6 mmol) are initially introduced in a 500 ml four-necked flask, and a solution of 50 g of bromo-4-tert-butylphenyl (234.6 mmol) in 200 ml of THF is slowly added dropwise. The reaction mixture is heated at the boil for 1.5 h and subsequently cooled to room temperature. Cyanogen chloride (18.8 g, 102 mmol) in 200 ml of THF is initially introduced in a second flask and cooled to 0° C. The cooled Grignard reagent is added dropwise at this temperature, and the mixture is stirred at room temperature for 12 h. After this time, 150 ml of HCl are added to the reaction mixture, and the aqueous phase is extracted three times with dichloromethane. The combined organic phases are washed with water, dried over Na$_2$SO$_4$ and evaporated. The residue is recrystallised from ethanol. The yield is 31 g (81.6 mmol, 80%).

Example 2

2,4-Bis(3-bromophenyl)-6-phenyl-1,3,5-triazine

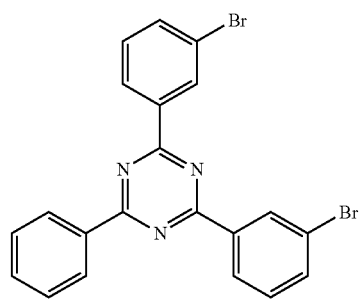 [SMILES: Brc1cccc(-c2nc(-c3ccccc3)nc(-c3cccc(Br)c3)n2)c1]

49 ml (392 mmol) of benzoyl chloride, 52.3 g (392 mmol) of AlCl$_3$ and 8.5 ml of thionyl chloride are initially introduced in 500 ml of 1,2-dichlorobenzene under protective-gas atmosphere. 150 g (824 mmol) of 3-bromobenzonitrile, dissolved in 300 ml of 1,2-dichlorobenzene, are added dropwise to this solution at room temperature via a dropping funnel, the mixture is subsequently stirred at 100° C. for 1 h, then stirred at 40° C. for 18 h. After this time, 1.5 l of methanol are added to the reaction mixture, and the residue is separated. The residue is washed by stirring with hot methanol, giving 59 g (126 mmol) (32%) of the product.

Example 3

2,4-Bisbiphenyl-3-yl-6-chloro-1,3,5-triazine

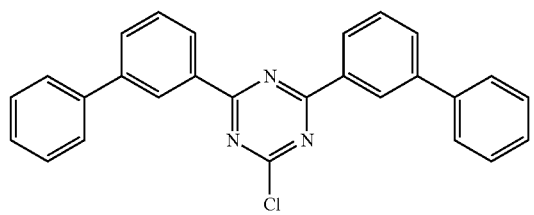 [SMILES: Clc1nc(-c2cccc(-c3ccccc3)c2)nc(-c2cccc(-c3ccccc3)c2)n1]

5.2 g of magnesium (0.215 mol) are initially introduced in a 500 ml four-necked flask, and a solution of 50 g of bromobiphenyl (214 mmol) in 200 ml of THF is slowly added dropwise. The reaction mixture is heated at the boil for 1.5 h and subsequently cooled to room temperature. Cyanogen chloride (17.2 g, 93 mmol) in 150 ml of THF is initially introduced in a second flask and cooled to 0° C. The cooled Grignard reagent then added dropwise at this temperature, and the mixture is stirred at RT for 12 h. After this time, 150 of HCl are added to the reaction mixture, and the aqueous phase is extracted three times with dichloromethane. The combined organic phases are washed with water, dried over Na$_2$SO$_4$ and evaporated. The residue is recrystallised from EtOH. The yield is 32.8 g (78 mmol, 84%).

Example 4

2-Chloro-4,6-bis[1,1'; 3',1"]terphenyl-5'-yl-1,3,5-triazine

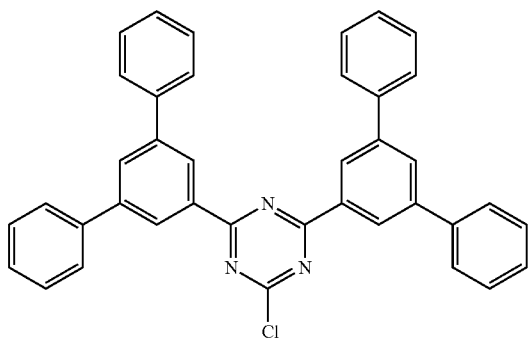 [SMILES: Clc1nc(-c2cc(-c3ccccc3)cc(-c3ccccc3)c2)nc(-c2cc(-c3ccccc3)cc(-c3ccccc3)c2)n1]

3.93 g of magnesium (162 mmol) are initially introduced in a 500 ml four-necked flask, and a solution of 50 g of 5'-bromo[1,1"; 3",1"]terphenyl (162 mmol) in 150 ml of THF is slowly added dropwise. The reaction mixture is heated at the boil for 1.5 h and subsequently cooled to room temperature. Cyanogen chloride (13 g, 70 mmol) in 150 ml of THF is initially introduced in a second flask and cooled to 0° C. The cooled Grignard reagent is added dropwise at this temperature, and the mixture is stirred at room temperature for 12 h. After this time, 150 ml of HCl are added to the reaction mixture, and the aqueous phase is extracted three times with dichloromethane. The combined organic phases are washed with water, dried over Na$_2$SO$_4$ and evaporated. The residue is recrystallised from EtOH. The yield is 27.8 g (49 mol, 70%).

Example 5

2-Chloro-4,6-bis(3-([3,1'; 5,1"]terphen-1-yl)phen-1-yl)-1,3,5-triazine

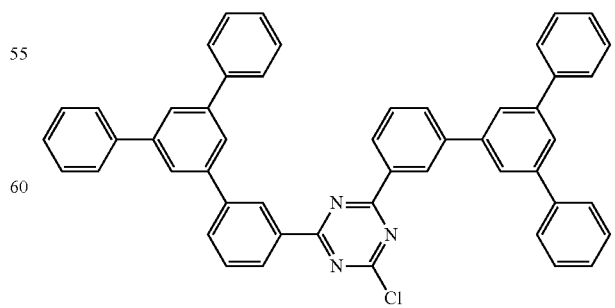

2.0 g of magnesium (81 mmol) are initially introduced in a 500 ml four-necked flask, and a solution of 31.2 g of 5'-(3-bromophenyl)[1,1'; 3',1"]terphenyl (81 mmol) in 100 ml of THF is slowly added dropwise. The reaction mixture is heated at the boil for 1.5 h and subsequently cooled to room temperature. Cyanogen chloride (6.4 g, 35 mmol) in 50 ml of THF is initially introduced in a second flask and cooled to 0° C. The cooled Grignard reagent is added dropwise at this temperature, and the mixture is stirred at room temperature for 12 h. After this time, 150 ml of HCl are added to the reaction mixture, the aqueous phase is extracted three times with dichloromethane. The combined organic phases are washed with water and dried over Na₂SO₄ and evaporated. The residue is recrystallised from toluene. The yield is 6.8 g (9.4 mmol, 28%).

Example 6

3-[3-(4,6-Diphenyl-1,3,5-triazin-2-yl)phenyl]-9-phenyl-9H-carbazole

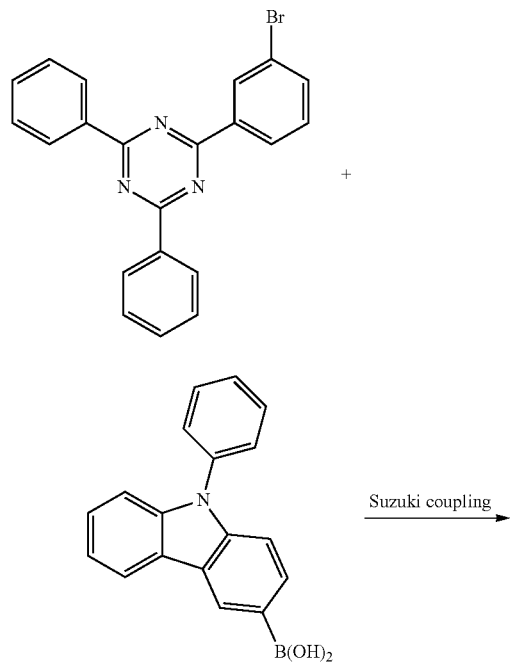

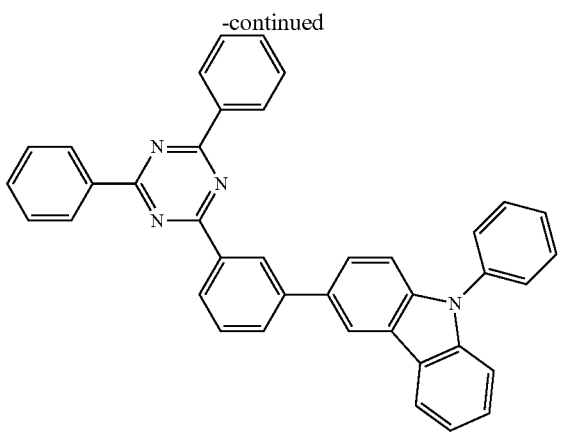

28.2 g (110.0 mmol) of (9-phenyl-9H-carbazol-3-yl)boronic acid, 42.6 g (110.0 mmol) of 2-(3-bromophenyl)-4,6-diphenyl-1.3.5-triazine and 44.6 g (210.0 mmol) of tripotassium phosphate are suspended in 500 ml of toulene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum (p=5×10⁻⁷ mbar). The purity is 99.9% (HPLC). The yield is 52 g (94 mmol), corresponding to 86% of theory.

The following compounds are obtained analogously:

| | Starting material 1 | Starting material 2 |
|---|---|---|
| 6a | (structure: 2-(3-bromophenyl)-4,6-diphenyl-1,3,5-triazine) 864377-31-1 | (structure: 9-phenyl-9H-carbazol-2-yl boronic acid) 1001911-63-2 |

6b 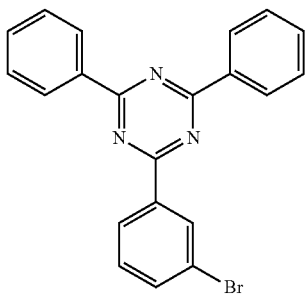
864377-31-1
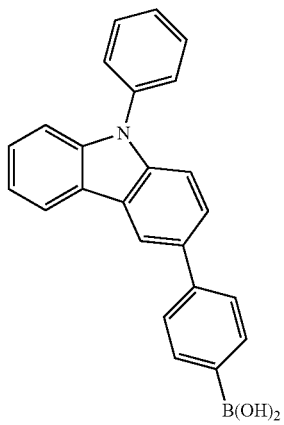
40963-55-6
6c 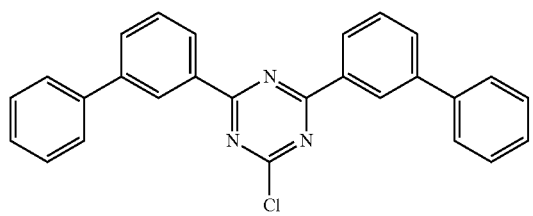 [SMILES: Clc1nc(-c2cccc(-c3ccccc3)c2)nc(-c2cccc(-c3ccccc3)c2)n1]
854952-60-6
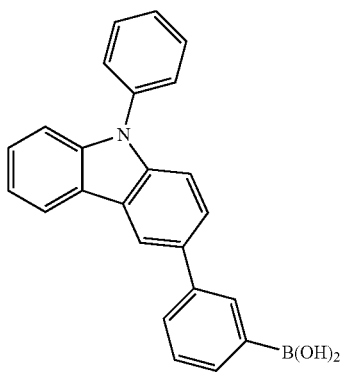
6d 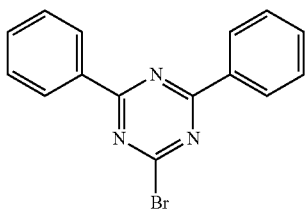
80984-72-8
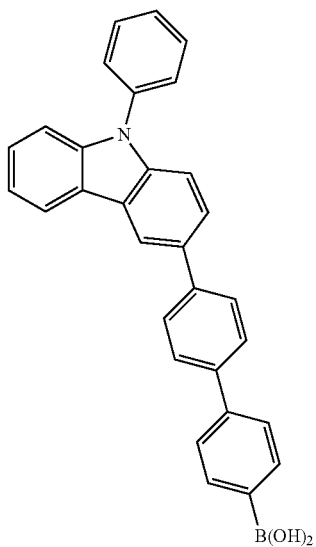
1267247-78-8

6e 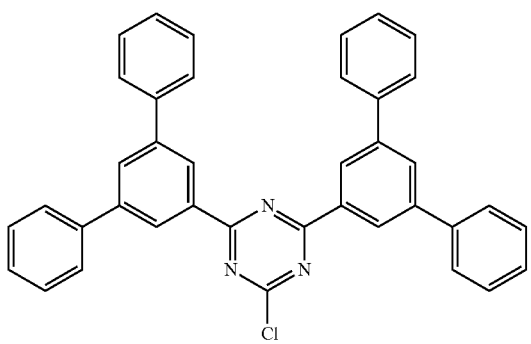 [SMILES: Clc1nc(-c2cc(-c3ccccc3)cc(-c3ccccc3)c2)nc(-c2cc(-c3ccccc3)cc(-c3ccccc3)c2)n1]
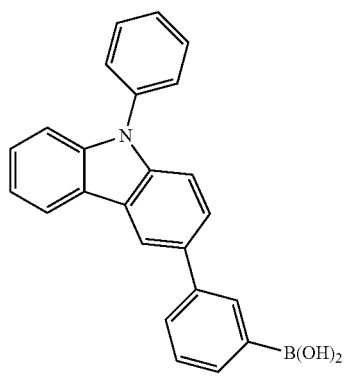
854952-60-6
6f 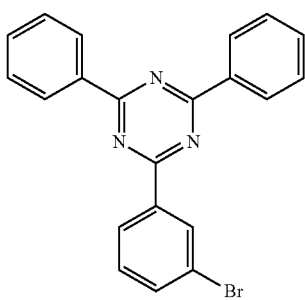
864377-31-1
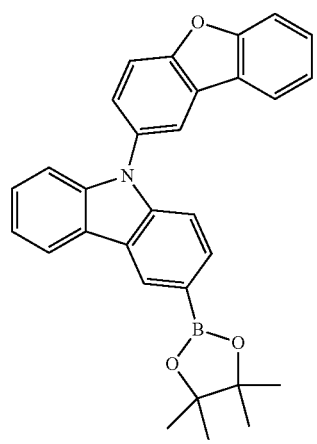
1338488-91-7
6g 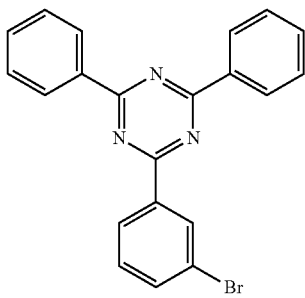
864377-31-1
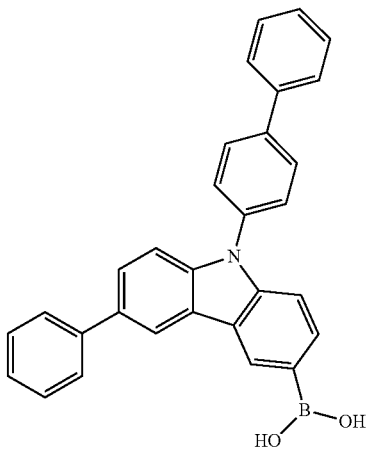
1316311-18-8

6h 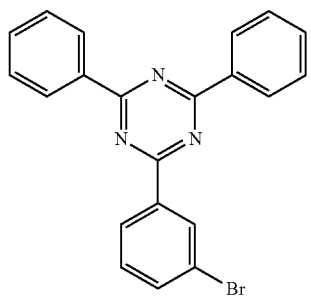
864377-31-1
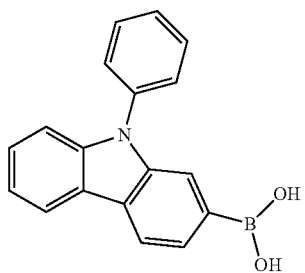
1001911-63-2
6i 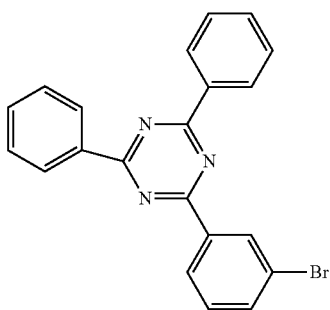
864377-31-1
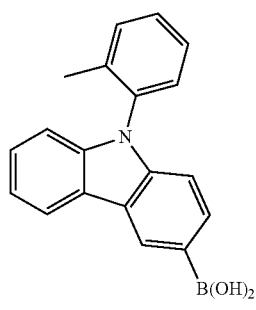
1133057-95-0
6j 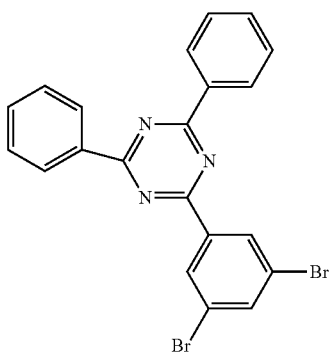
1073062-59-5
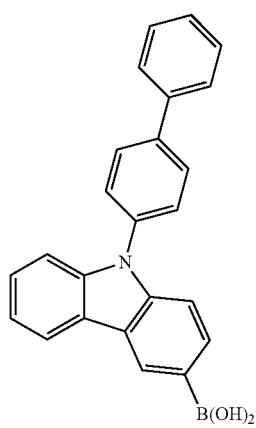
1028648-22-7
6k 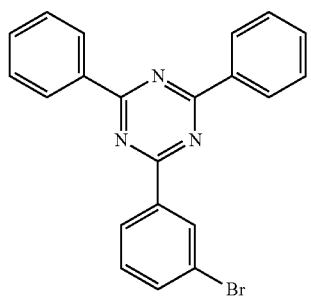
864377-31-1
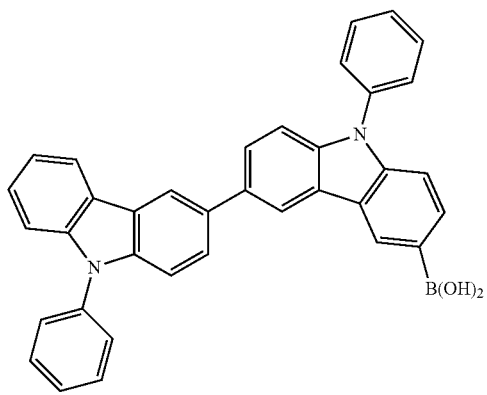
918137-86-7

-continued
6l
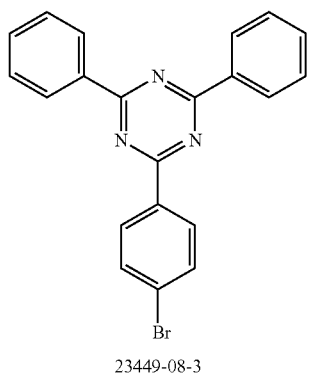 [SMILES: Brc1ccc(-c2nc(-c3ccccc3)nc(-c3ccccc3)n2)cc1]
23449-08-3
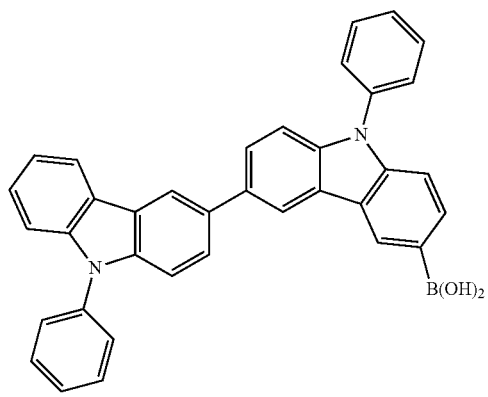
918137-86-7
6m
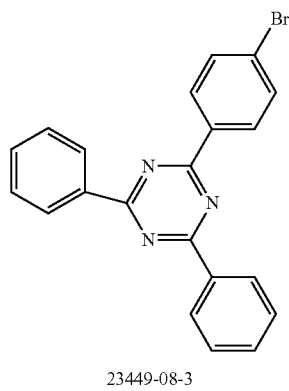 [SMILES: Brc1ccc(-c2nc(-c3ccccc3)nc(-c3ccccc3)n2)cc1]
23449-08-3
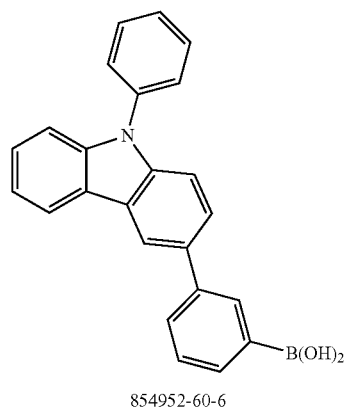 [SMILES: OB(O)c1cccc(-c2ccc3c(c2)c2ccccc2n3-c2ccccc2)c1]
854952-60-6
6n
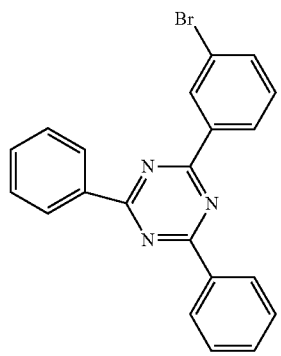
64377-31-1
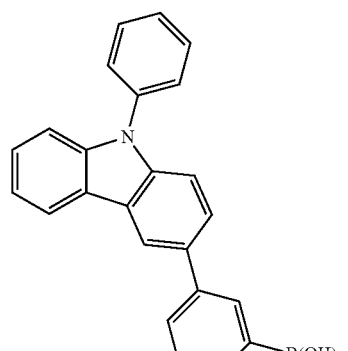
854952-60-6

-continued
6o
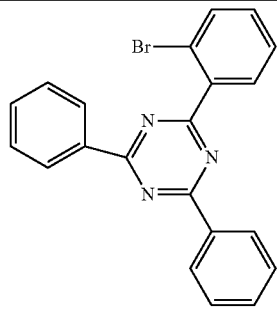
77989-15-2
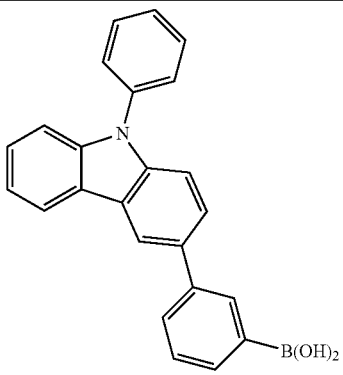
854952-60-6
6p
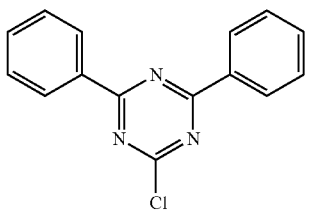
80984-79-8
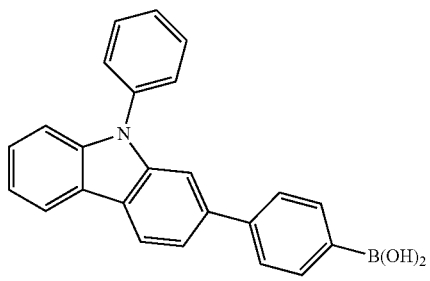
1365118-40-6
6q
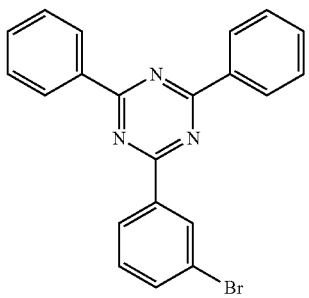
64377-31-1
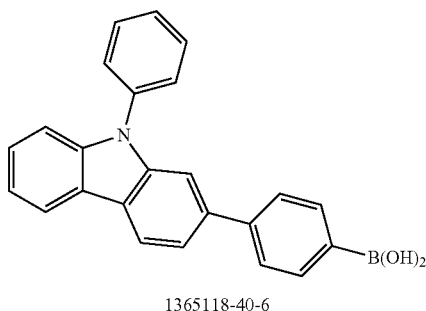 [SMILES: OB(O)c1ccc(-c2ccc3c4ccccc4n(-c4ccccc4)c3c2)cc1]
1365118-40-6
6r
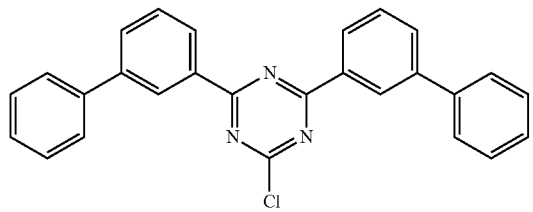 [SMILES: Clc1nc(-c2cccc(-c3ccccc3)c2)nc(-c2cccc(-c3ccccc3)c2)n1]
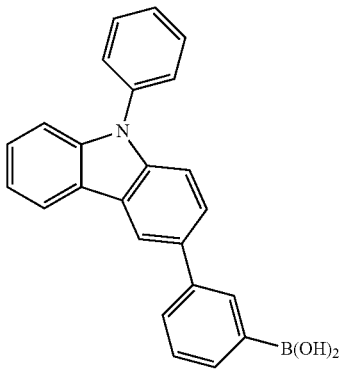 [SMILES: OB(O)c1cccc(-c2ccc3c(c2)c2ccccc2n3-c2ccccc2)c1]

-continued
6s
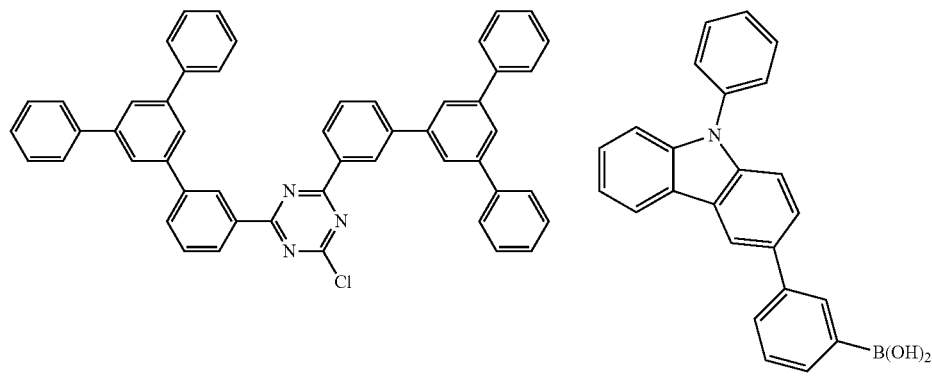
6t
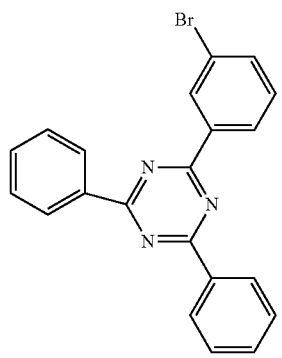
64377-31-1
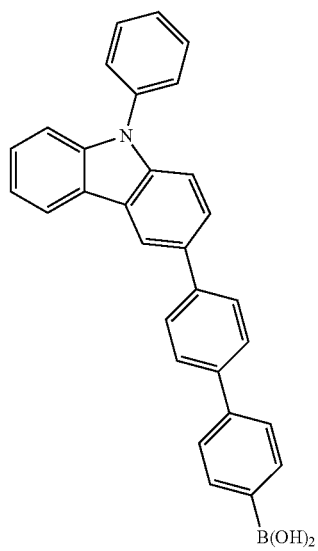
1267247-78-8
6u
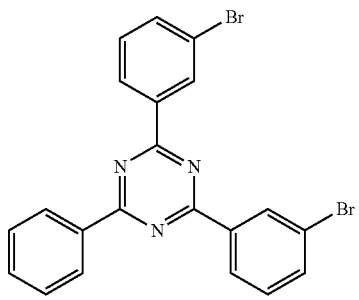 [SMILES: Brc1cccc(-c2nc(-c3ccccc3)nc(-c3cccc(Br)c3)n2)c1]
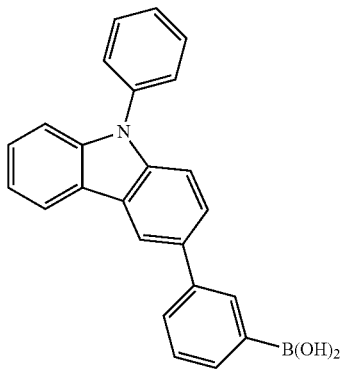 [SMILES: OB(O)c1cccc(-c2ccc3c(c2)c2ccccc2n3-c2ccccc2)c1]

-continued

| Product | Yield |
|---|---|
| 6a (structure) | 79% |
| 6b (structure) | 81% |
| 6c (structure) | 83% |

| | | |
|---|---|---|
| 6d | 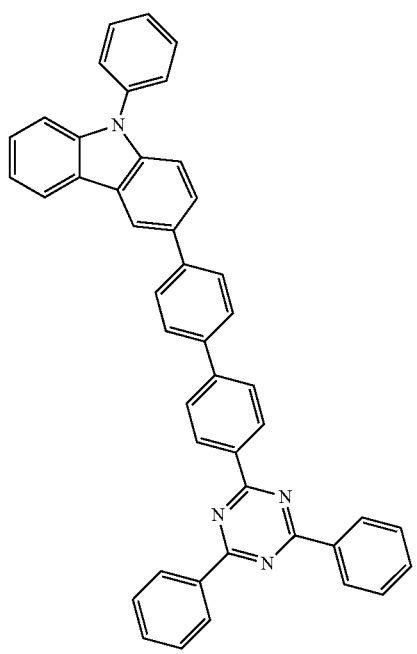 [SMILES: c1ccc(-c2nc(-c3ccccc3)nc(-c3ccc(-c4ccc(-c5ccc6c(c5)c5ccccc5n6-c5ccccc5)cc4)cc3)n2)cc1] | 77% |
| 6e | 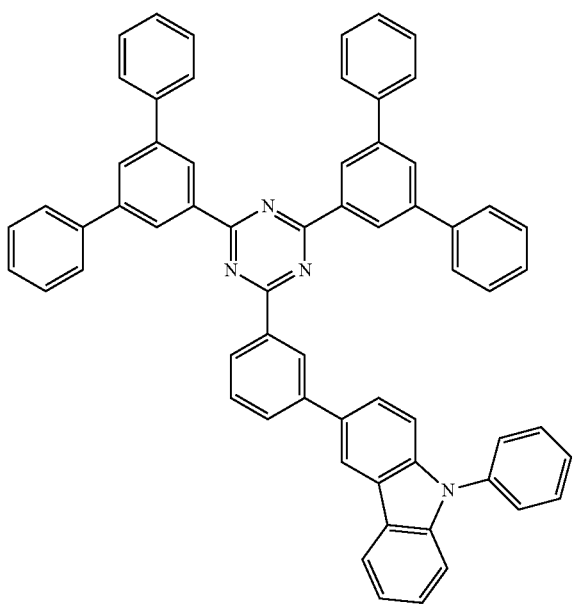 [SMILES: c1ccc(-c2cc(-c3ccccc3)cc(-c3nc(-c4cccc(-c5ccc6c(c5)c5ccccc5n6-c5ccccc5)c4)nc(-c4cc(-c5ccccc5)cc(-c5ccccc5)c4)n3)c2)cc1] | 88% |

| | | |
|---|---|---|
| 6f | 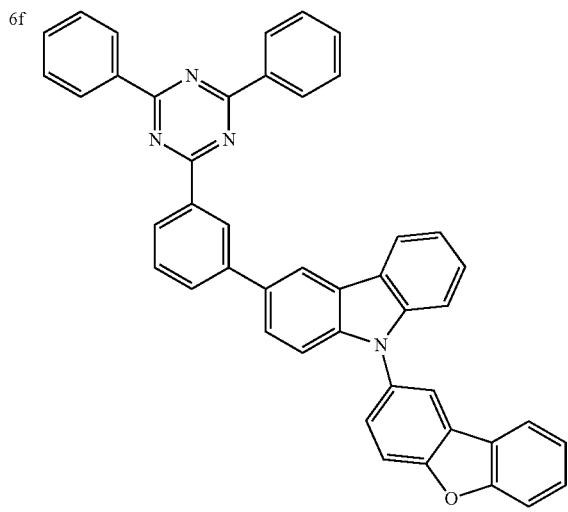 | 76% |
| 6g | 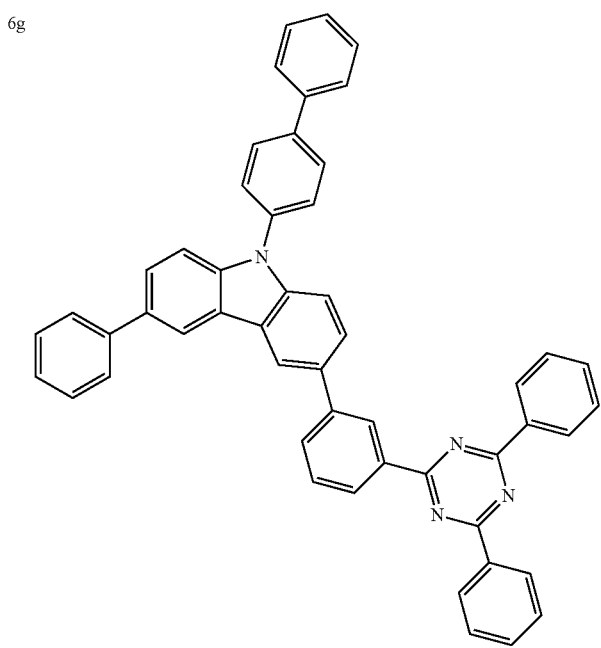 | 73% |

| | | |
|---|---|---|
| 6h | 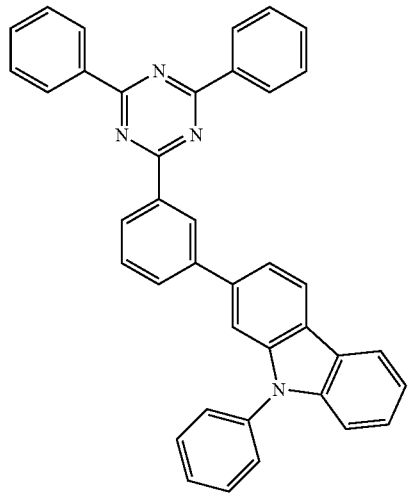 864377-31-1 | 88% |
| 6i | 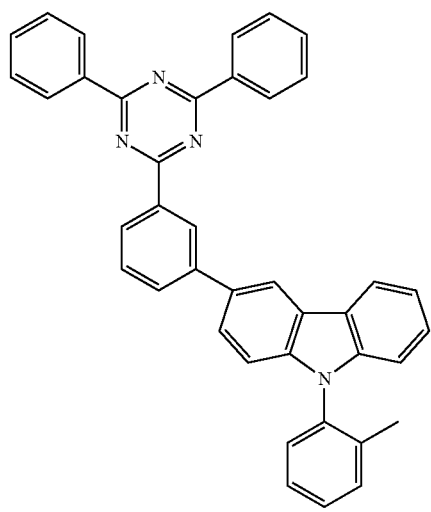 [SMILES: Cc1ccccc1-n1c2ccccc2c2cc(-c3cccc(-c4nc(-c5ccccc5)nc(-c5ccccc5)n4)c3)ccc21] | 76% |
| 6j | 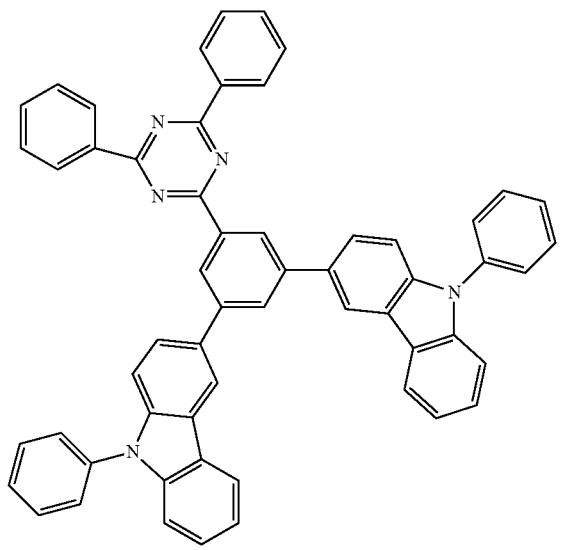 [SMILES: c1ccc(-c2nc(-c3ccccc3)nc(-c3cc(-c4ccc5c(c4)c4ccccc4n5-c4ccccc4)cc(-c4ccc5c(c4)c4ccccc4n5-c4ccccc4)c3)n2)cc1] | 72% |

6k 89%
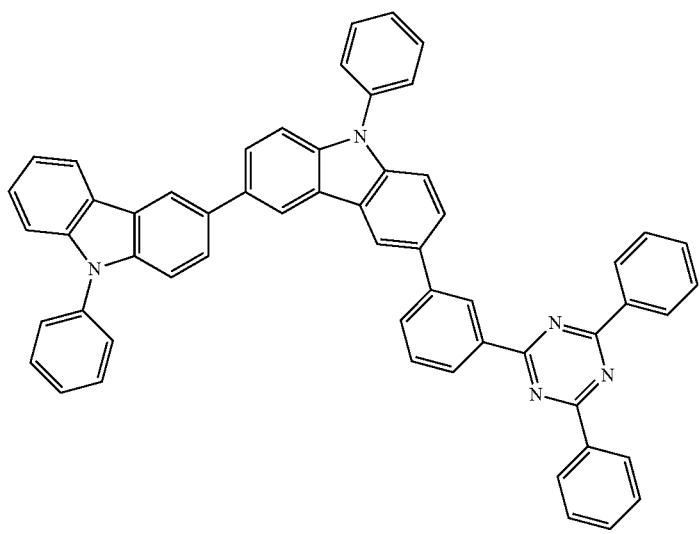 [SMILES: c1ccc(-c2nc(-c3ccccc3)nc(-c3cccc(-c4ccc5c(c4)c4cc(-c6ccc7c(c6)c6ccccc6n7-c6ccccc6)ccc4n5-c4ccccc4)c3)n2)cc1]
6l 77%
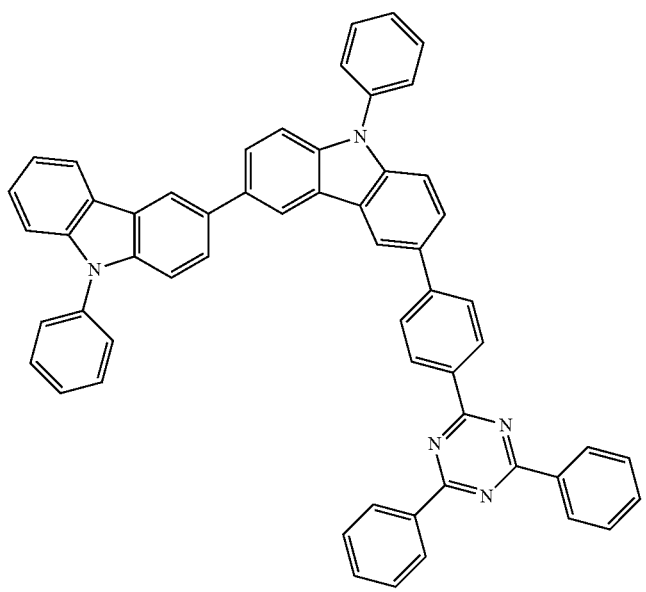 [SMILES: c1ccc(-c2nc(-c3ccccc3)nc(-c3ccc(-c4ccc5c(c4)c4cc(-c6ccc7c(c6)c6ccccc6n7-c6ccccc6)ccc4n5-c4ccccc4)cc3)n2)cc1]
6m 85%
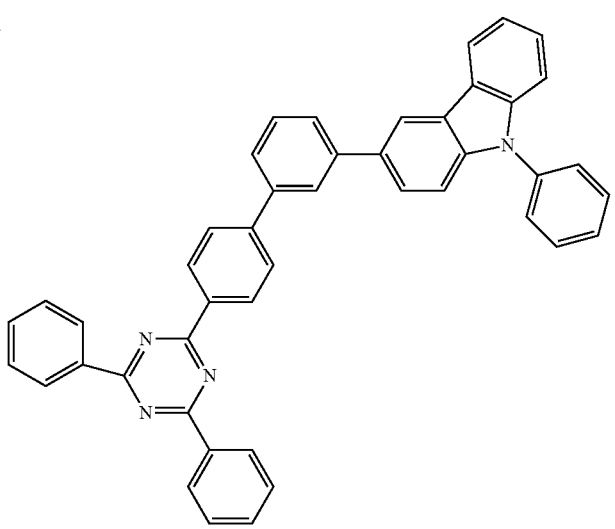 [SMILES: c1ccc(-c2nc(-c3ccccc3)nc(-c3ccc(-c4cccc(-c5ccc6c(c5)c5ccccc5n6-c5ccccc5)c4)cc3)n2)cc1]

| | | |
|---|---|---|
| 6n | 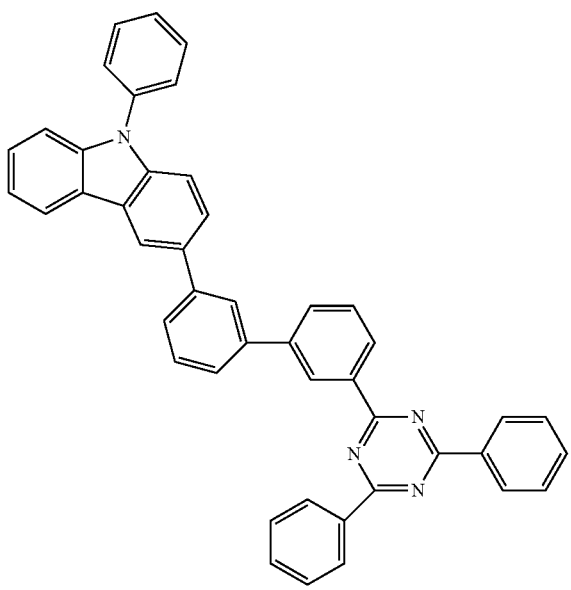 [SMILES: c1ccc(-c2nc(-c3ccccc3)nc(-c3cccc(-c4cccc(-c5ccc6c(c5)c5ccccc5n6-c5ccccc5)c4)c3)n2)cc1] | 76% |
| 6o | 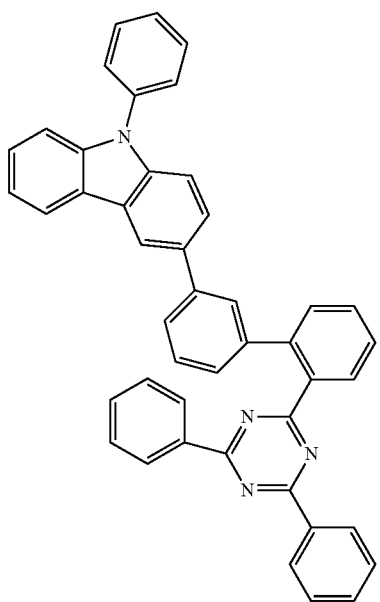 [SMILES: c1ccc(-c2nc(-c3ccccc3)nc(-c3ccccc3-c3cccc(-c4ccc5c(c4)c4ccccc4n5-c4ccccc4)c3)n2)cc1] | 68% |
| 6p | 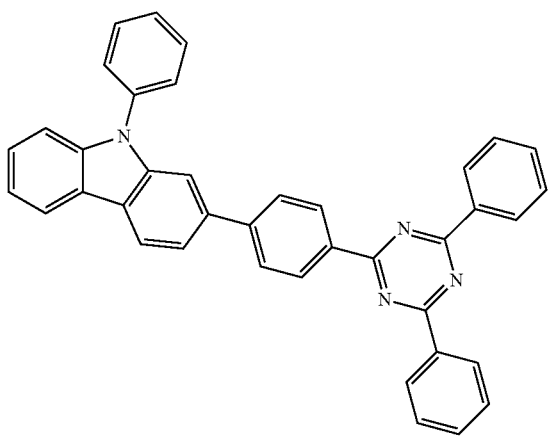 [SMILES: c1ccc(-c2nc(-c3ccccc3)nc(-c3ccc(-c4ccc5c6ccccc6n(-c6ccccc6)c5c4)cc3)n2)cc1] | 78% |

6q 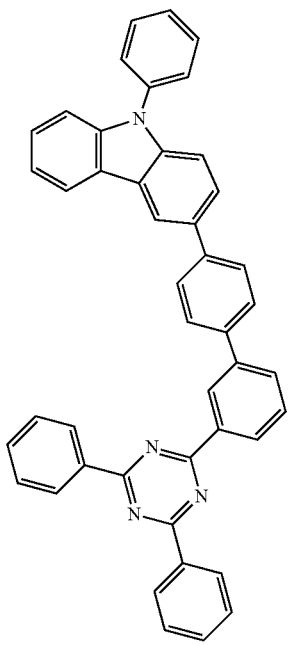 [SMILES: c1ccc(-c2nc(-c3ccccc3)nc(-c3cccc(-c4ccc(-c5ccc6c(c5)c5ccccc5n6-c5ccccc5)cc4)c3)n2)cc1] 69%
6r 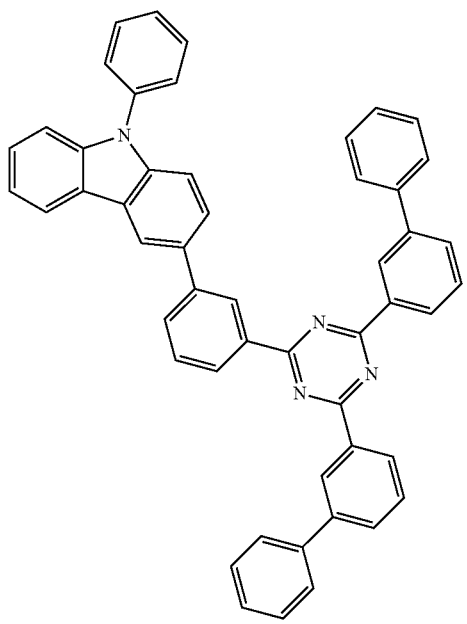 [SMILES: c1ccc(-c2cccc(-c3nc(-c4cccc(-c5ccccc5)c4)nc(-c4cccc(-c5ccc6c(c5)c5ccccc5n6-c5ccccc5)c4)n3)c2)cc1] 84%

| 6s | 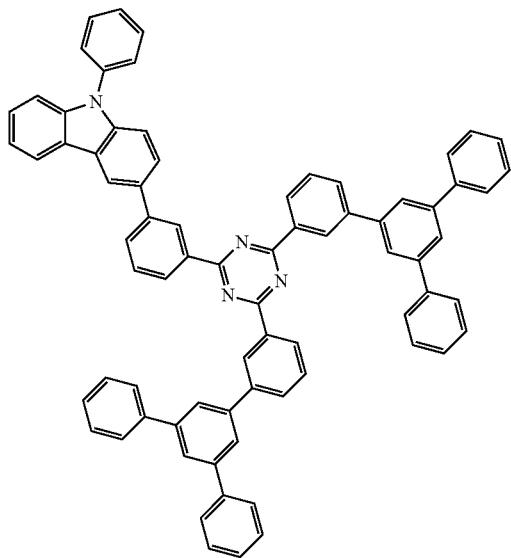 [SMILES: c1ccc(-c2cc(-c3ccccc3)cc(-c3cccc(-c4nc(-c5cccc(-c6cc(-c7ccccc7)cc(-c7ccccc7)c6)c5)nc(-c5cccc(-c6ccc7c(c6)c6ccccc6n7-c6ccccc6)c5)n4)c3)c2)cc1] | 80% |
| 6t | 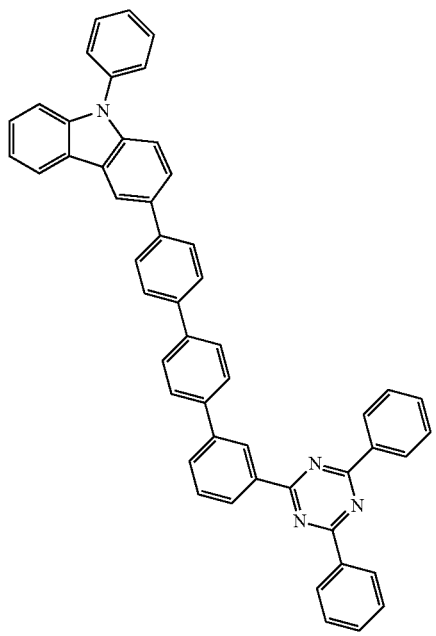 [SMILES: c1ccc(-c2nc(-c3ccccc3)nc(-c3cccc(-c4ccc(-c5ccc(-c6ccc7c(c6)c6ccccc6n7-c6ccccc6)cc5)cc4)c3)n2)cc1] | 79% |

| 6u | 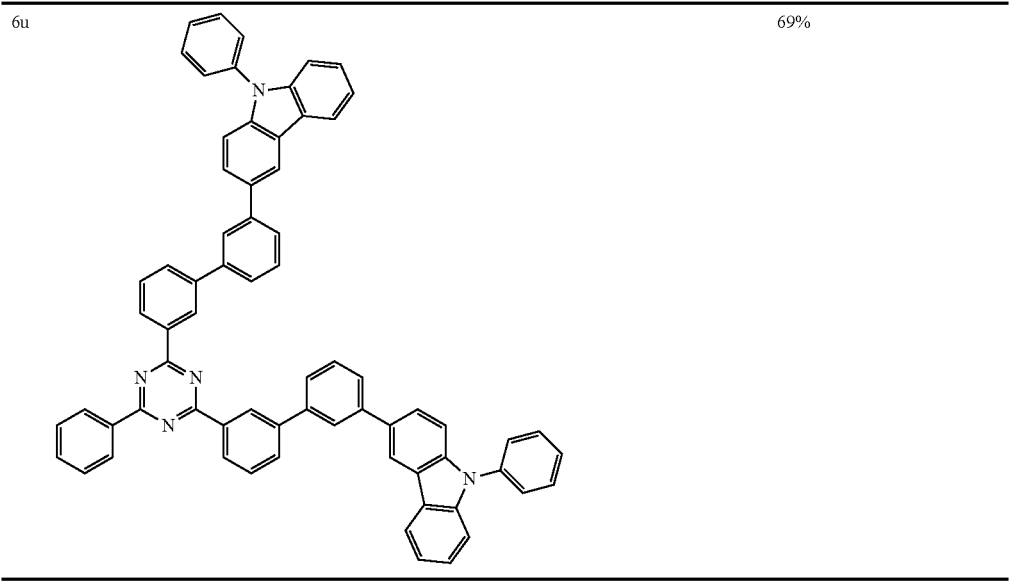 | 69% |

Example 7

3-(5-Bromobiphenyl-3-yl)-9-phenyl-9H-carbazole

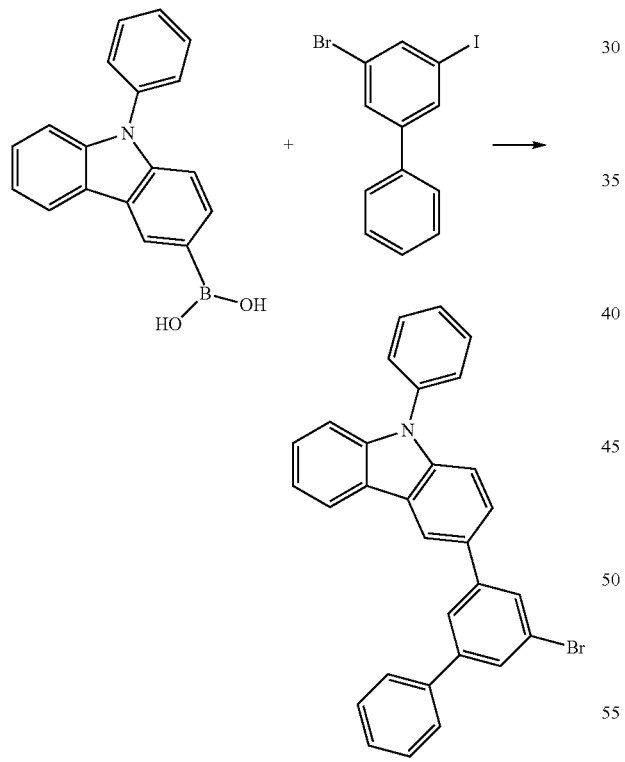

15.5 g (43.3 mmol) of 3-bromo-5-iodobiphenyl and 13.7 g (48 mmol) of (9-phenyl-9H-carbazol-3-yl)boronic acid are dissolved in 80 ml of toluene and degassed. 281 ml of a degassed 2M $K_2CO_3$ solution and 2.5 g (2.2 mmol) of $Pd(OAc)_2$ are added. The reaction mixture is subsequently stirred at 80° C. for 48 h under a protective-gas atmosphere. The cooled solution is diluted with toluene, washed a number of times with water, dried and evaporated. The product is purified by column chromatography on silica gel with toluene/heptane (1:2). The purity is 98%. Yield: 17.6 g (37 mmol, 78%) of theory.

The following compounds are obtained analogously:
| | Starting material 1 | Starting material 2 | Product | Yield |
|---|---|---|---|---|
| 7a | 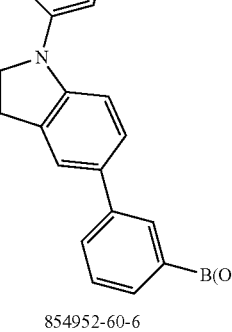<br>854952-60-6 | 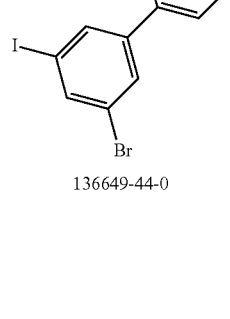<br>136649-44-0 | 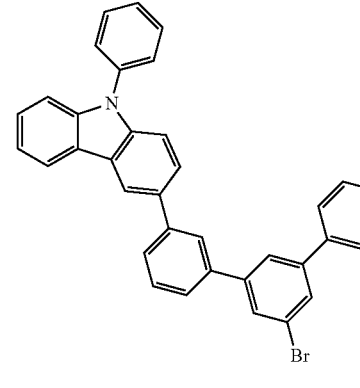 | 70% |
| 7b | 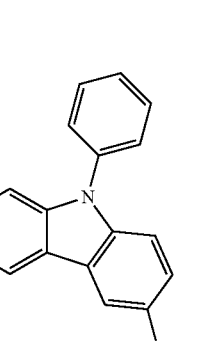<br>854952-58-2 | 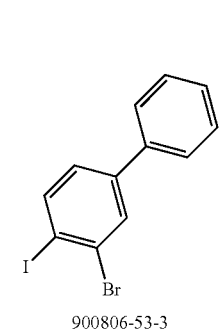 [SMILES: Brc1cc(-c2ccccc2)ccc1I]<br>900806-53-3 | 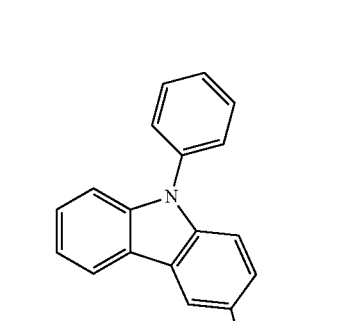 | 69% |
| 7c | 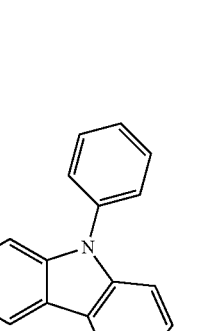<br>854952-58-2 | 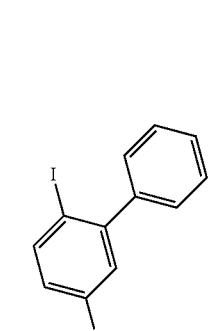<br>4510-78-5 | 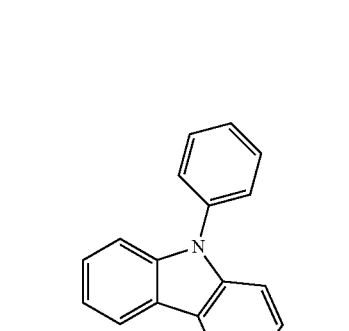 | 68% |

-continued

| Starting material 1 | Starting material 2 | Product | Yield |
|---|---|---|---|
| 7d 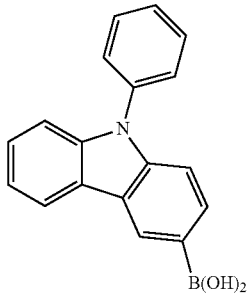 854952-58-2 | 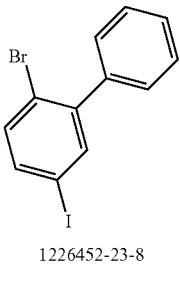 [SMILES: Brc1ccc(I)cc1-c1ccccc1] 1226452-23-8 | 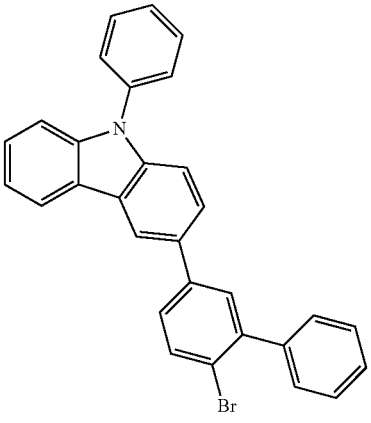 [SMILES: Brc1ccc(-c2ccc3c(c2)c2ccccc2n3-c2ccccc2)cc1-c1ccccc1] | 83% |

Example 8

3-(5-Boronobiphenyl-3-yl)-9-phenyl-9H-carbazole

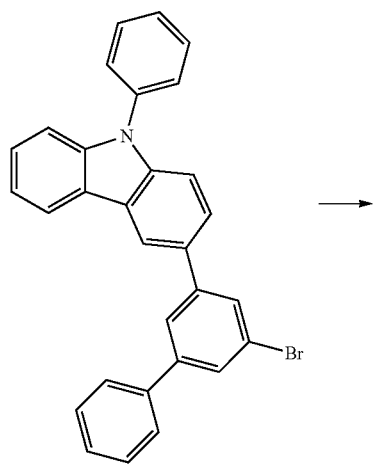

→

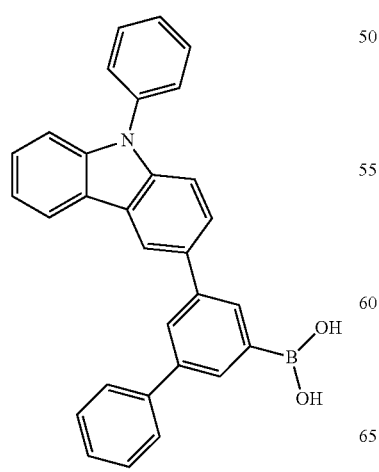

110 ml (276 mmol) of n-buthyllithium (2.5 M in hexane) are added dropwise to a solution, cooled to −78° C., of 128 g (270 mmol) of 3-(5-bromobiphenyl-3-yl)-9-phenyl-9-H-carbazole in 1500 ml of diethyl ether. The reaction mixture is stirred at −78° C. for 30 min. The mixture is allowed to come to room temperature, re-cooled to −78° C., and a mixture of 40 ml (351 mmol) of trimethyl borate in 50 ml of diethyl ether is then added rapidly. After warming to −10° C., the mixture is hydrolysed using 135 ml of 2 N hydrochloric acid. The organic phase is separated off, washed with water, dried over sodium sulfate and evaporated to dryness. The residue is taken up in 300 ml of n-heptane, the colourless solid is filtered off with suction, washed with n-heptane and dried in vacuo. Yield: 112 g (256 mmol), 95% of theory.

The following compounds are obtained analogously:
| | Starting material 1 | Product | Yield |
|---|---|---|---|
| 8a | 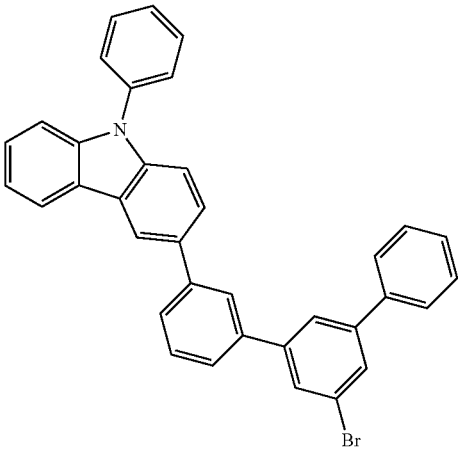 [SMILES: Brc1cc(-c2ccccc2)cc(-c2cccc(-c3ccc4c(c3)c3ccccc3n4-c3ccccc3)c2)c1] | 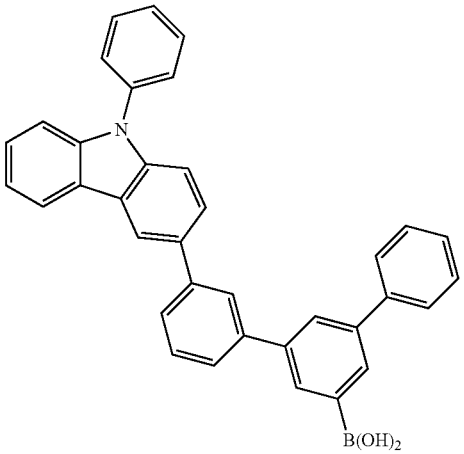 [SMILES: OB(O)c1cc(-c2ccccc2)cc(-c2cccc(-c3ccc4c(c3)c3ccccc3n4-c3ccccc3)c2)c1] | 64% |
| 8b | 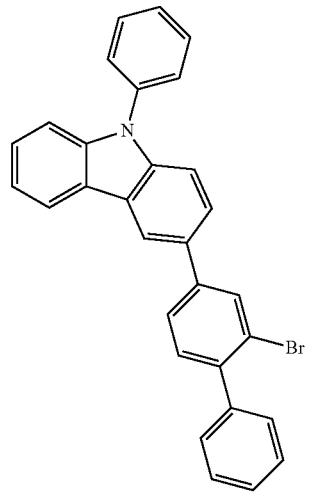 [SMILES: Brc1cc(-c2ccc3c(c2)c2ccccc2n3-c2ccccc2)ccc1-c1ccccc1] | 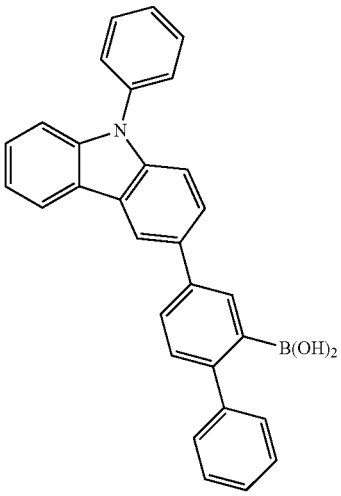 [SMILES: OB(O)c1cc(-c2ccc3c(c2)c2ccccc2n3-c2ccccc2)ccc1-c1ccccc1] | 60% |
| 8c | 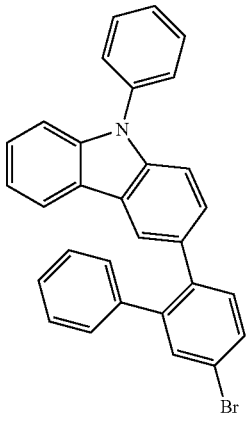 [SMILES: Brc1ccc(-c2ccc3c(c2)c2ccccc2n3-c2ccccc2)c(-c2ccccc2)c1] | 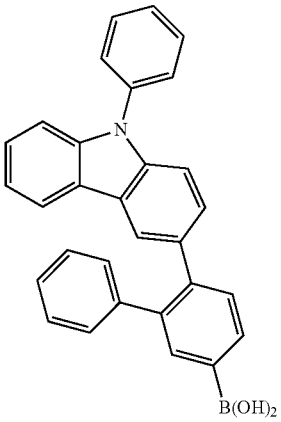 [SMILES: OB(O)c1ccc(-c2ccc3c(c2)c2ccccc2n3-c2ccccc2)c(-c2ccccc2)c1] | 63% |

-continued

| Starting material 1 | Product | Yield |
|---|---|---|
| 8d | | 69% |
| 8e  1190100-35-6 | | 59% |
| 8f  1345970-20-8 | | 83% |

| Starting material 1 | Product | Yield |
|---|---|---|
| 8g 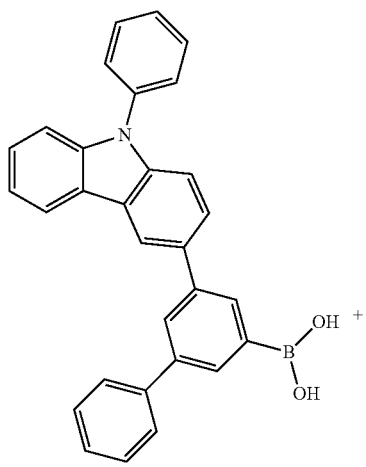 | 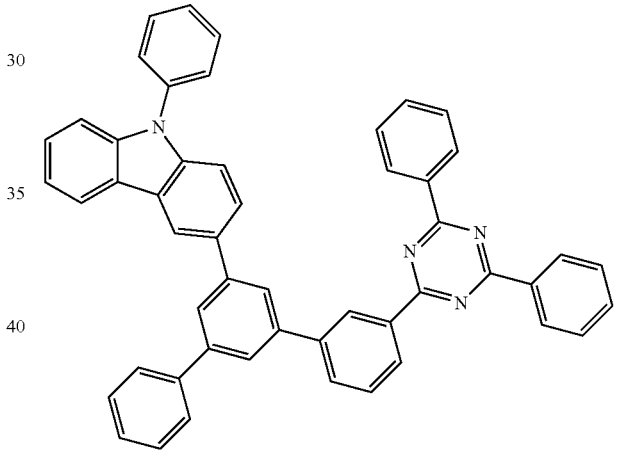 | 73% |

Example 9

3-[3''-(4,6-Diphenyl-1,3,5-triazin-2-yl)[1,1'; 3',1'']terphenyl-5'-yl]-9-phenyl-9H-carbazole

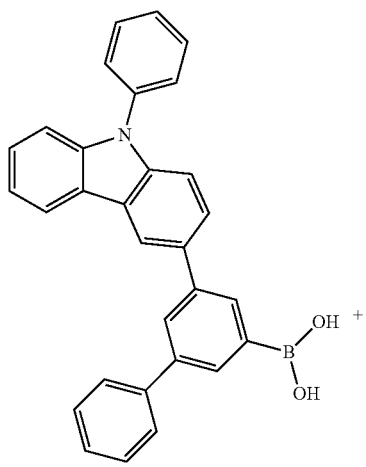

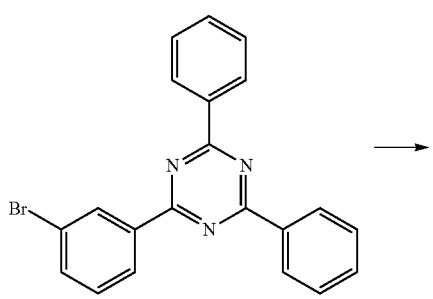

→

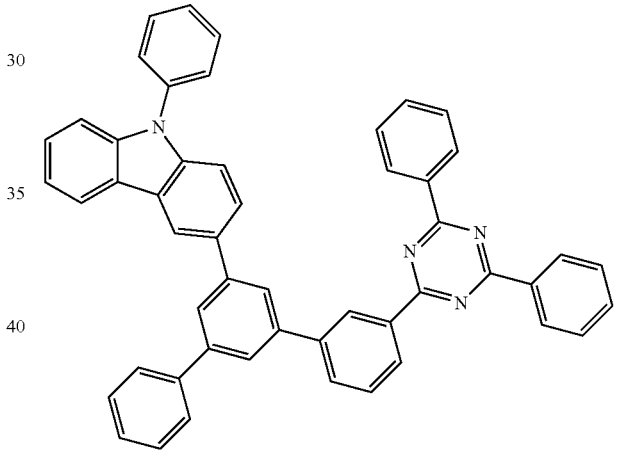

2.47 g (8.1 mmol) of tetrakistriphenylphosphinopalladium(0) are added to a vigorously stirred suspension of 15.5 g (40 mmol) of 2-(3-bromophenyl)-4,6-diphenyl-1,3,5-triazine, 17.5 g (40 mmol) of 3-(5-boronobiphenyl-3-yl)-9-phenyl-9H-carbazole and 63.9 g (127 mmol) of $Na_2CO_3$ in 500 ml of DMF, and the mixture is subsequently heated under reflux for 16 h. After cooling, the solid which has precipitated out is filtered off with suction, washed three times with 50 ml of toluene, three times with 50 ml of ethanol:water (1:1, v:v) and three times with 100 ml of ethanol and recrystallised three times from DMF (about 15 ml/g). and finally sublimed in a high vacuum ($p=5\times10^{-7}$ mbar). Yield 27 g (38 mmol), 85.0% of theory; purity 99.9% (HPLC)

The following compounds are obtained analogously:
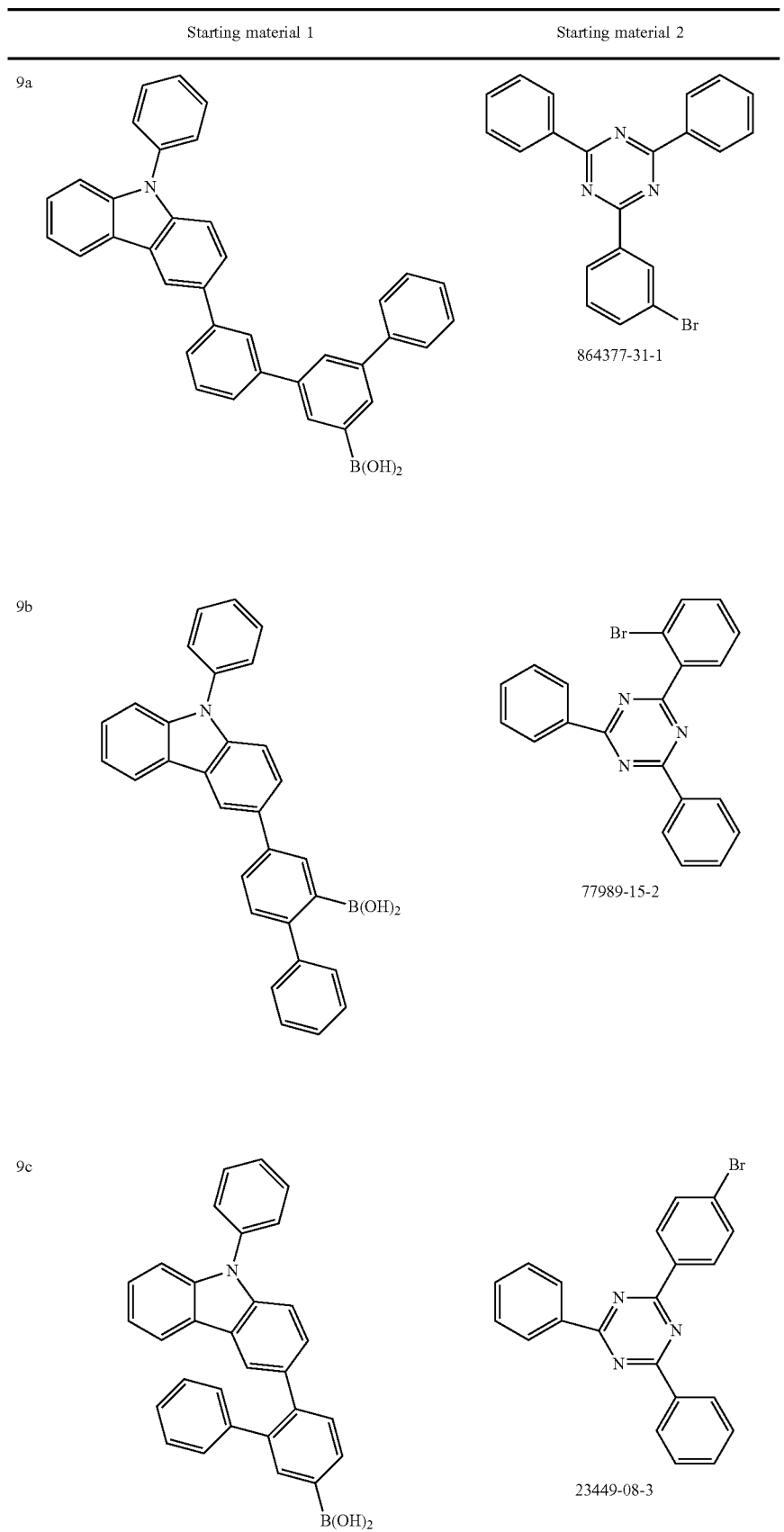

| | | |
|---|---|---|
| 9d | 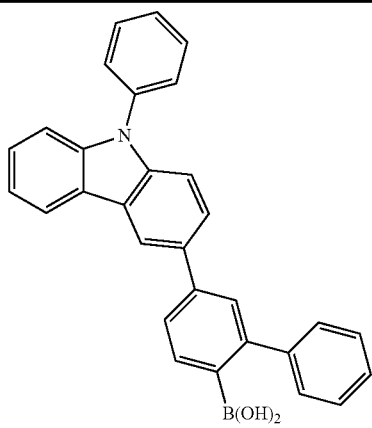 | 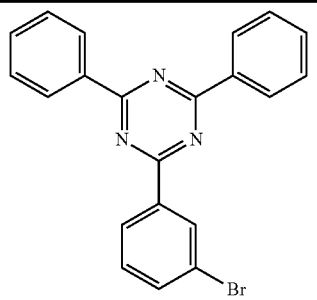
864377-31-1 |
| 9e | 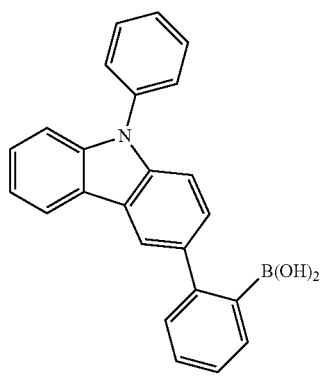 [SMILES: OB(O)c1ccccc1-c1ccc2c(c1)c1ccccc1n2-c1ccccc1] | 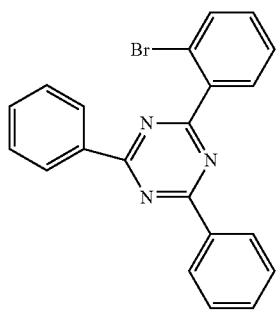
77989-15-2 |
| 9f | 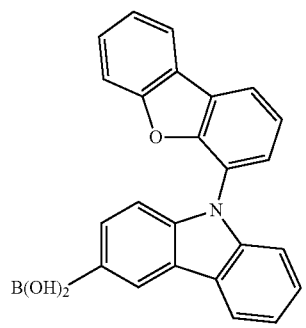 [SMILES: OB(O)c1ccc2c(c1)c1ccccc1n2-c1cccc2c1oc1ccccc12] | 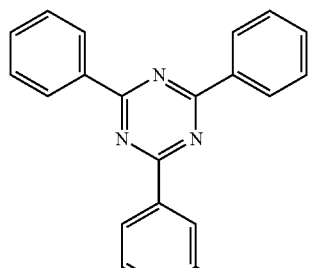
864377-31-1 |
| 9g | 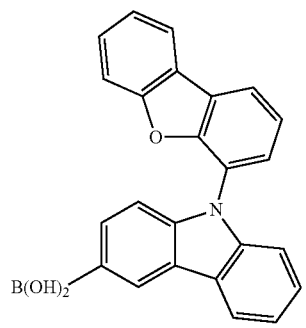 [SMILES: OB(O)c1ccc2c(c1)c1ccccc1n2-c1cccc2c1oc1ccccc12] | 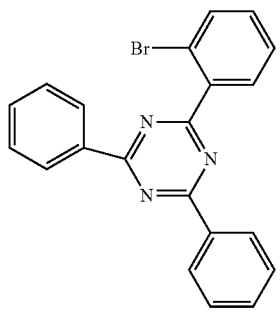
77989-15-2 |

9h 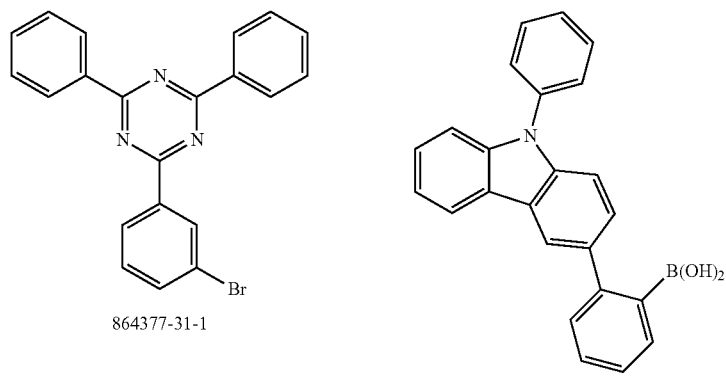
864377-31-1
9i 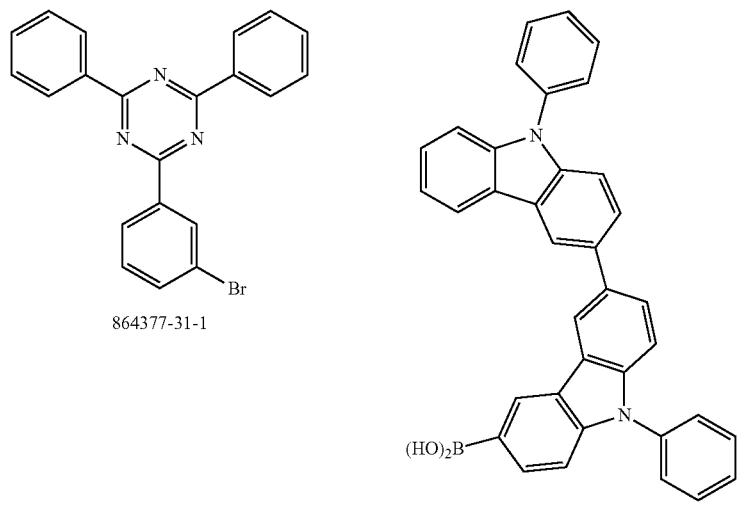
864377-31-1
| Product | Yield |
|---|---|
| 9a 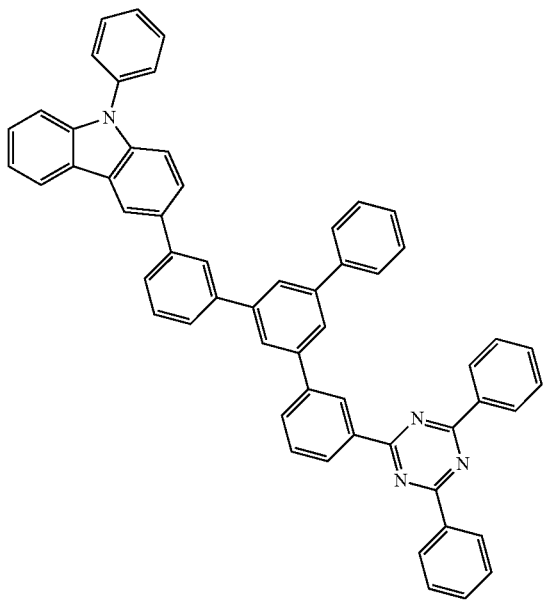 [SMILES: c1ccc(-c2cc(-c3cccc(-c4ccc5c(c4)c4ccccc4n5-c4ccccc4)c3)cc(-c3cccc(-c4nc(-c5ccccc5)nc(-c5ccccc5)n4)c3)c2)cc1] | 86% |

| | |
|---|---|
| 9b 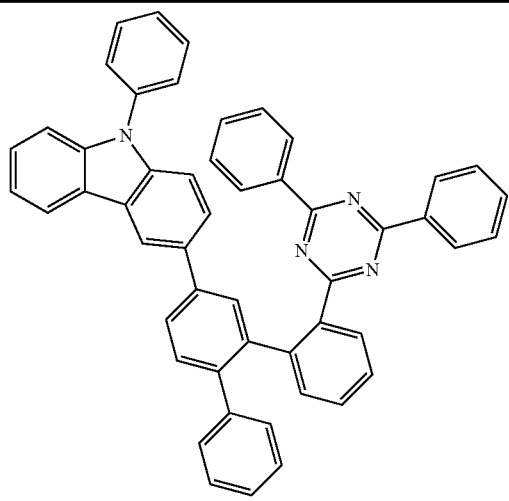 | 67% |
| 9c 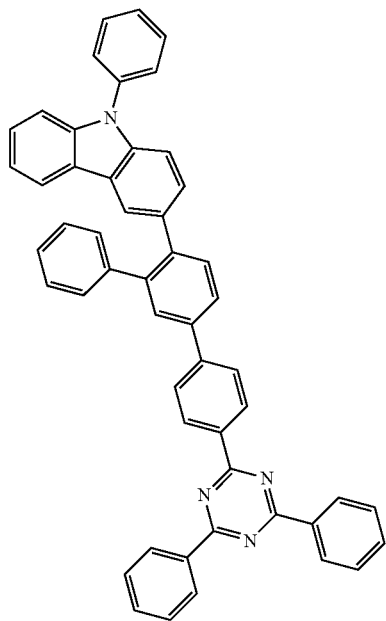 [SMILES: c1ccc(-c2nc(-c3ccccc3)nc(-c3ccc(-c4ccc(-c5ccc6c(c5)c5ccccc5n6-c5ccccc5)c(-c5ccccc5)c4)cc3)n2)cc1] | 69% |

| | | |
|---|---|---|
| 9d | 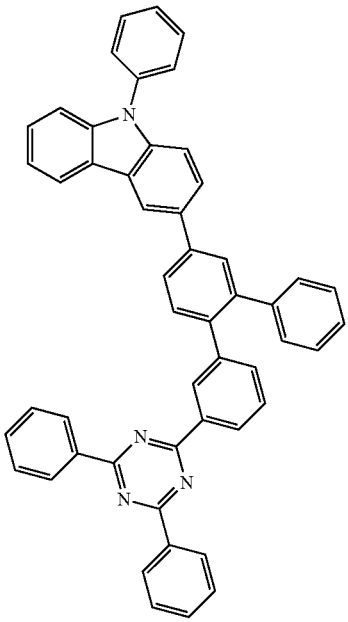 [SMILES: c1ccc(-c2nc(-c3ccccc3)nc(-c3cccc(-c4ccc(-c5ccc6c(c5)c5ccccc5n6-c5ccccc5)cc4-c4ccccc4)c3)n2)cc1] | 76% |
| 9e | 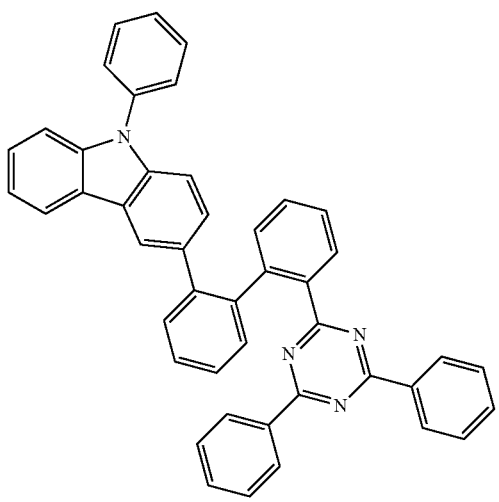 [SMILES: c1ccc(-c2nc(-c3ccccc3)nc(-c3ccccc3-c3ccccc3-c3ccc4c(c3)c3ccccc3n4-c3ccccc3)n2)cc1] | 82% |
| 9f | 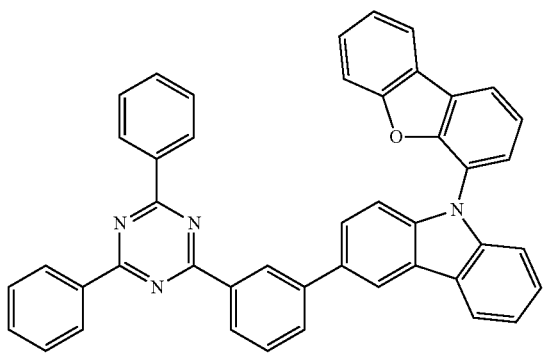 [SMILES: c1ccc(-c2nc(-c3ccccc3)nc(-c3cccc(-c4ccc5c(c4)c4ccccc4n5-c4cccc5c4oc4ccccc45)c3)n2)cc1] | 80% |

| | | |
|---|---|---|
| 9g | 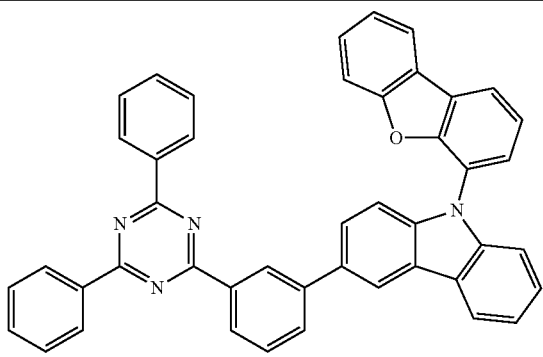 | 64% |
| 9h | 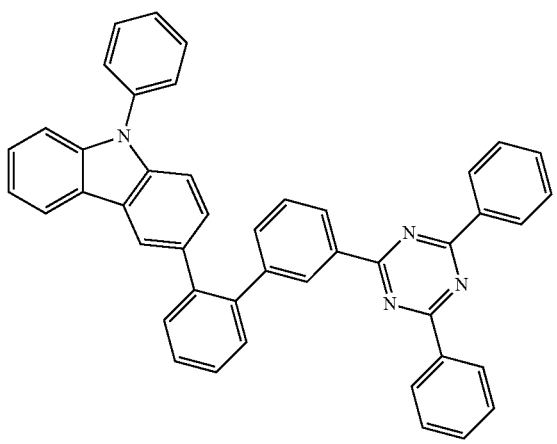 [SMILES: c1ccc(-c2nc(-c3ccccc3)nc(-c3cccc(-c4ccccc4-c4ccc5c(c4)c4ccccc4n5-c4ccccc4)c3)n2)cc1] | 73% |
| 9i | 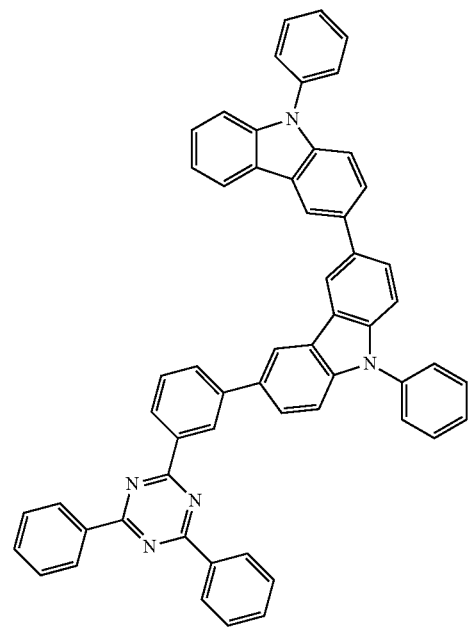 [SMILES: c1ccc(-c2nc(-c3ccccc3)nc(-c3cccc(-c4ccc5c(c4)c4cc(-c6ccc7c(c6)c6ccccc6n7-c6ccccc6)ccc4n5-c4ccccc4)c3)n2)cc1] | 71% |

Example

Production of OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in the following Examples V1 to E17 (see Tables 1 and 2). Glass plates coated with structured ITO (indium tin oxide) in a thickness of 50 nm are coated with 20 nm of PEDOT:PSS (poly-(3,4-ethylenedioxythiophene) poly(styrenesulfonate), purchased as CLEVIOS™ P VP AI 4083 from Heraeus Precious Metals GmbH, Germany, applied by spin coating from aqueous solution) for improved processing. These coated glass plates form the substrates to which the OLEDs are applied. The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium cathode with a thickness of 100 nm. The precise structure of the OLEDs is shown in Table 1. The materials required for the production of the OLEDs are shown in Table 3. Furthermore, a reference such as "6a" here relates to the material mentioned in Example 6a described above. This also applies analogously to all other compounds according to the invention.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as H1:VCbz1:TEG1 (55%:35%:10%) here means that material H1 is present in the layer in a proportion by volume of 55%, VCbz1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$. Finally, EQE1000 denotes the external quantum efficiency at an operating luminous density of 1000 cd/m$^2$. The lifetime LT is defined as the time after which the luminous density drops to a certain proportion L1 from the initial luminous density L0 on operation at constant current. An expression of L0=10000 cd/m$^2$ and L1=80% in Table X2 means that the lifetime indicated in column LT corresponds to the time after which the initial luminous density drops from 10000 cd/m$^2$ to 8000 cd/m$^2$.

The data of the various OLEDs are summarised in Table 2. Example V1-V6 are OLEDs comprising materials in accordance with the prior art, Examples E1-E17 show data of OLEDs comprising materials according to the invention.

Some of the examples are explained in greater detail below in order to illustrate the advantages of the compounds according to the invention. However, it should be pointed out that this only represents a selection of the data shown in Table 2. As can be seen from the table, improvements compared with the prior art are also achieved on use of the compounds according to the invention which are not described in greater detail, in some cases in all parameters, but in some cases only an improvement of efficiency or voltage or lifetime is observed. However, even the improvement of one of the said parameters represents a significant advance, since various applications require optimisation with respect to different parameters.

Use of Compounds According to the Invention as Matrix Materials in Phosphorescent OLEDs In combination with the green-emitting dopant TEG1, materials according to the invention exhibit significant improvements compared with the prior art. A power efficiency which is improved by up to 15% (Examples V1 and E3) and a 40% better lifetime (Examples V2 and E3) are obtained.

If two materials are used as a mixture with dopant TEG1 in the EML, a lifetime which is improved by about 30% and an approximately 20% higher power efficiency are obtained with material 6n according to the invention in combination with VCbz1 compared with the use of H2 with VCbz1 (Examples V4 and E10).

Similarly good improvements are also obtained on use of the red-emitting dopant TER1 (Examples V6 and E17).

The materials according to the invention thus give rise to significant improvements compared with the prior art on use as matrix materials in phosphorescent OLEDs.

Use of Compounds According to the Invention as Electron-Transport Materials

On use of compound 6n according to the invention as electron-transport material, significantly lower voltage and better efficiency are obtained than with substance H3 in accordance with the prior art (Examples V5 and E16).

TABLE 1

Structure of the OLEDs

| Ex. | HTL Thickness | IL Thickness | EBL Thickness | EML Thickness | RBL Thickness | ETL Thickness | EIL Thickness |
|---|---|---|---|---|---|---|---|
| V1 | SpA1 70 nm | HATCN 5 nm | SpMA1 90 nm | H1:TEG1 (90%:10%) 30 nm | — | ST1:LiQ (50%:50%) 40 nm | — |
| V2 | SpA1 70 nm | HATCN 5 nm | SpMA1 90 nm | H2:TEG1 (90%:10%) 30 nm | — | ST1:LiQ (50%:50%) 40 nm | — |
| V3 | SpA1 70 nm | HATCN 5 nm | SpMA1 90 nm | H3:TEG1 (90%:10%) 30 nm | — | ST1:LiQ (50%:50%) 40 nm | — |

TABLE 1-continued

Structure of the OLEDs

| Ex. | HTL Thickness | IL Thickness | EBL Thickness | EML Thickness | RBL Thickness | ETL Thickness | EIL Thickness |
|---|---|---|---|---|---|---|---|
| V4 | SpA1 70 nm | HATCN 5 nm | SpMA1 90 nm | H2:VCbz1:TEG1 (45%:45%:10%) 30 nm | IC1 10 nm | ST1:LiQ (50%:50%) 30 nm | — |
| V5 | SpA1 70 nm | HATCN 5 nm | SpMA1 90 nm | IC1:TEG1 (90%:10%) 30 nm | — | H3 40 nm | LiQ 3 nm |
| V6 | SpA1 90 nm | HATCN 5 nm | SpMA1 130 nm | H1:TER1 (92%:8%) 40 nm | — | ST1:LiQ (50%:50%) 40 nm | — |
| E1 | SpA1 70 nm | HATCN 5nm | SpMA1 90 nm | 6:TEG1 (90%:10%) 30 nm | — | ST1:LiQ (50%:50%) 40 nm | — |
| E2 | SpA1 70 nm | HATCN 5 nm | SpMA1 90 nm | 6a:TEG1 (90%:10%) 30 nm | — | ST1:LiQ (50%:50%) 40 nm | — |
| E3 | SpA1 70 nm | HATCN 5 nm | SpMA1 90 nm | 6b:TEG1 (90%:10%) 30 nm | — | ST1:LiQ (50%:50%) 40 nm | — |
| E4 | SpA1 70 nm | HATCN 5 nm | SpMA1 90 nm | 6e:TEG1 (90%:10%) 30 nm | — | ST1:LiQ (50%:50%) 40 nm | — |
| E5 | SpA1 70 nm | HATCN 5 nm | SpMA1 90 nm | 6f:TEG1 (90%:10%) 30 nm | — | ST1:LiQ (50%:50%) 40 nm | — |
| E6 | SpA1 70 nm | HATCN 5 nm | SpMA1 90 nm | 6h:TEG1 (90%:10%) 30 nm | — | ST1:LiQ (50%:50%) 40 nm | — |
| E7 | SpA1 70 nm | HATCN 5 nm | SpMA1 90 nm | 6j:TEG1 (90%:10%) 30 nm | — | ST1:LiQ (50%:50%) 40 nm | — |
| E8 | SpA1 70 nm | HATCN 5 nm | SpMA1 90 nm | 6k:TEG1 (90%:10%) 30 nm | — | ST1:LiQ (50%:50%) 40 nm | — |
| E9 | SpA1 70 nm | HATCN 5 nm | SpMA1 90 nm | 6n:TEG1 (90%:10%) 30 nm | — | ST1:LiQ (50%:50%) 40 nm | — |
| E10 | SpA1 70 nm | HATCN 5 nm | SpMA1 90 nm | 6n:VCbz1:TEG1 (45%:45%:10%) 30 nm | IC1 10 nm | ST1:LiQ (50%:50%) 30 nm | — |
| E11 | SpA1 70 nm | HATCN 5 nm | SpMA1 90 nm | 6o:TEG1 (90%:10%) 30 nm | — | ST1:LiQ (50%:50%) 40 nm | — |
| E12 | SpA1 70 nm | HATCN 5 nm | SpMA1 90 nm | 6p:TEG1 (90%:10%) 30 nm | — | ST1:LiQ (50%:50%) 40 nm | — |
| E13 | SpA1 70nm | HATCN 5 nm | SpMA1 90 nm | 9:TEG1 (90%:10%) 30 nm | — | ST1:LiQ (50%:50%) 40 nm | — |
| E14 | SpA1 70 nm | HATCN 5 nm | SpMA1 90 nm | 9f:TEG1 (90%:10%) 30 nm | — | ST1:LiQ (50%:50%) 40 nm | — |
| E15 | SpA1 70 nm | HATCN 5 nm | SpMA1 90 nm | 9h:TEG1 (90%:10%) 30 nm | — | ST1:LiQ (50%:50%) 40 nm | — |
| E16 | SpA1 70 nm | HATCN 5 nm | SpMA1 90 nm | IC1:TEG1 (90%:10%) 30 nm | — | 6n 40 nm | LiQ 3 nm |
| E17 | SpA1 90 nm | HATCN 5 nm | SpMA1 130 nm | 6n:TER1 (92%:8%) 40 nm | — | ST1:LiQ (50%:50%) 40 nm | — |

TABLE 2

Data of the OLEDs

| Ex. | U1000 (V) | CE1000 (cd/A) | PE1000 (lm/W) | EQE 1000 | CIE x/y at 1000 cd/m² | L0 | L1 % | LT (h) |
|---|---|---|---|---|---|---|---|---|
| V1 | 4.0 | 55 | 43 | 15.3% | 0.33/0.62 | 10000 cd/m² | 80 | 65 |
| V2 | 4.1 | 44 | 34 | 12.3% | 0.32/0.62 | 10000 cd/m² | 80 | 110 |
| V3 | 4.9 | 56 | 36 | 15.6% | 0.33/0.62 | 10000 cd/m² | 80 | 105 |
| V4 | 4.0 | 50 | 39 | 13.8% | 0.33/0.62 | 10000 cd/m² | 80 | 240 |
| V5 | 4.4 | 53 | 38 | 14.7% | 0.33/0.62 | 10000 cd/m² | 80 | 90 |
| V6 | 4.6 | 9.3 | 6.4 | 9.8% | 0.67/0.33 | 4000 cd/m² | 80 | 290 |
| E1 | 4.2 | 56 | 42 | 15.5% | 0.32/0.62 | 10000 cd/m² | 80 | 85 |
| E2 | 4.2 | 55 | 41 | 15.3% | 0.33/0.63 | 10000 cd/m² | 80 | 115 |
| E3 | 3.7 | 59 | 50 | 16.5% | 0.32/0.62 | 10000 cd/m² | 80 | 155 |
| E4 | 4.4 | 54 | 39 | 15.0% | 0.33/0.62 | 10000 cd/m² | 80 | 130 |
| E5 | 4.1 | 58 | 44 | 16.1% | 0.33/0.62 | 10000 cd/m² | 80 | 120 |
| E6 | 4.3 | 51 | 38 | 14.3% | 0.33/0.62 | 10000 cd/m² | 80 | 110 |
| E7 | 4.0 | 57 | 45 | 15.9% | 0.33/0.62 | 10000 cd/m² | 80 | 135 |
| E8 | 4.8 | 53 | 35 | 14.8% | 0.33/0.63 | 10000 cd/m² | 80 | 90 |
| E9 | 4.0 | 60 | 47 | 16.8% | 0.33/0.62 | 10000 cd/m² | 80 | 140 |
| E10 | 3.8 | 57 | 47 | 15.8% | 0.33/0.62 | 10000 cd/m² | 80 | 305 |
| E11 | 4.2 | 59 | 44 | 16.4% | 0.33/0.62 | 10000 cd/m² | 80 | 140 |
| E12 | 4.1 | 57 | 44 | 15.9% | 0.32/0.63 | 10000 cd/m² | 80 | 110 |
| E13 | 4.1 | 59 | 45 | 16.3% | 0.33/0.62 | 10000 cd/m² | 80 | 130 |
| E14 | 3.7 | 55 | 46 | 15.2% | 0.33/0.62 | 10000 cd/m² | 80 | 105 |
| E15 | 4.2 | 60 | 45 | 16.6% | 0.33/0.62 | 10000 cd/m² | 80 | 135 |
| E16 | 3.2 | 59 | 58 | 16.5% | 0.33/0.62 | 10000 cd/m² | 80 | 110 |

TABLE 2-continued
Data of the OLEDs
| Ex. | U1000 (V) | CE1000 (cd/A) | PE1000 (lm/W) | EQE 1000 | CIE x/y at 1000 cd/m² | L0 | L1 % | LT (h) |
|---|---|---|---|---|---|---|---|---|
| E17 | 4.5 | 10.8 | 7.6 | 11.7% | 0.67/0.33 | 4000 cd/m² | 80 | 360 |
TABLE 3
Structural formulae of the materials for the OLEDs
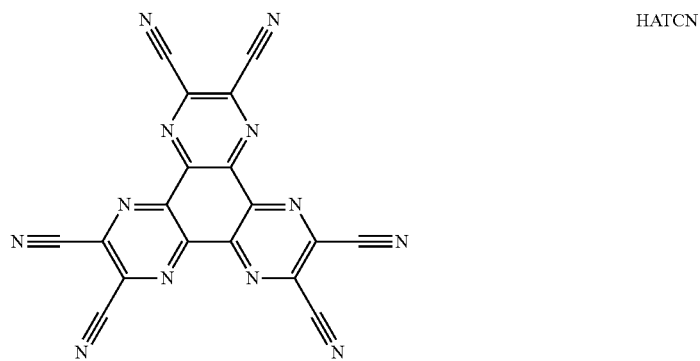
HATCN
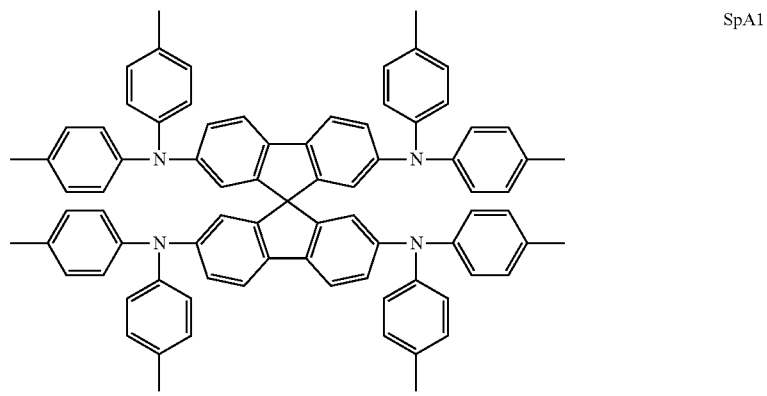
SpA1
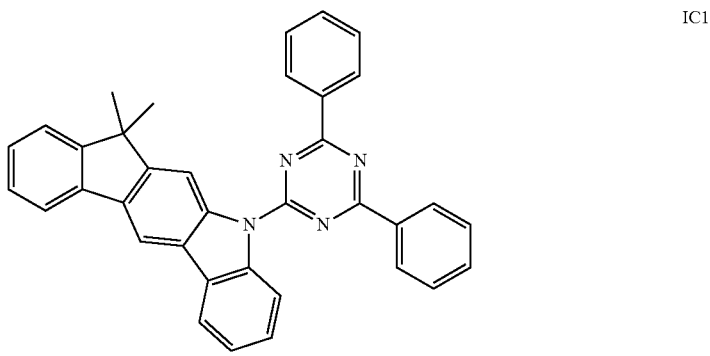
IC1

TABLE 3-continued
Structural formulae of the materials for the OLEDs
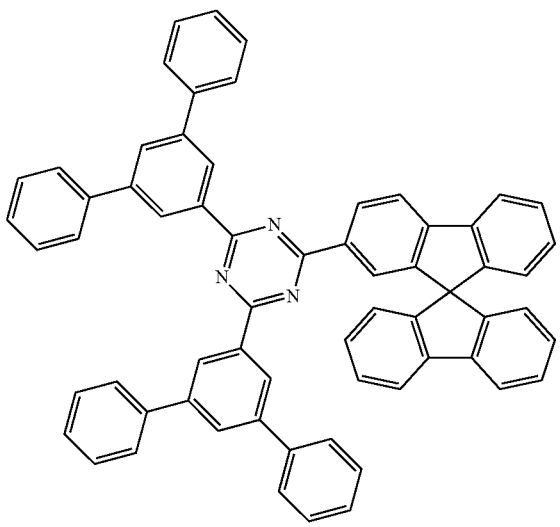 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST1
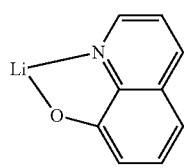
LiQ
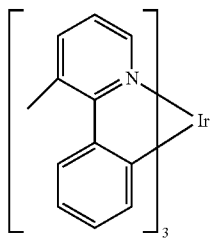
TEG1
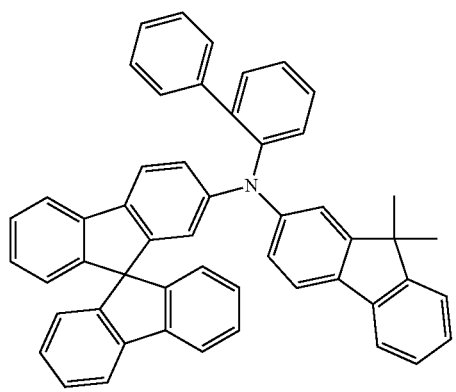 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
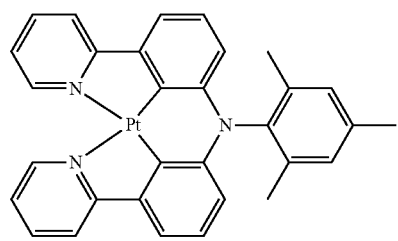
TER1

TABLE 3-continued
Structural formulae of the materials for the OLEDs
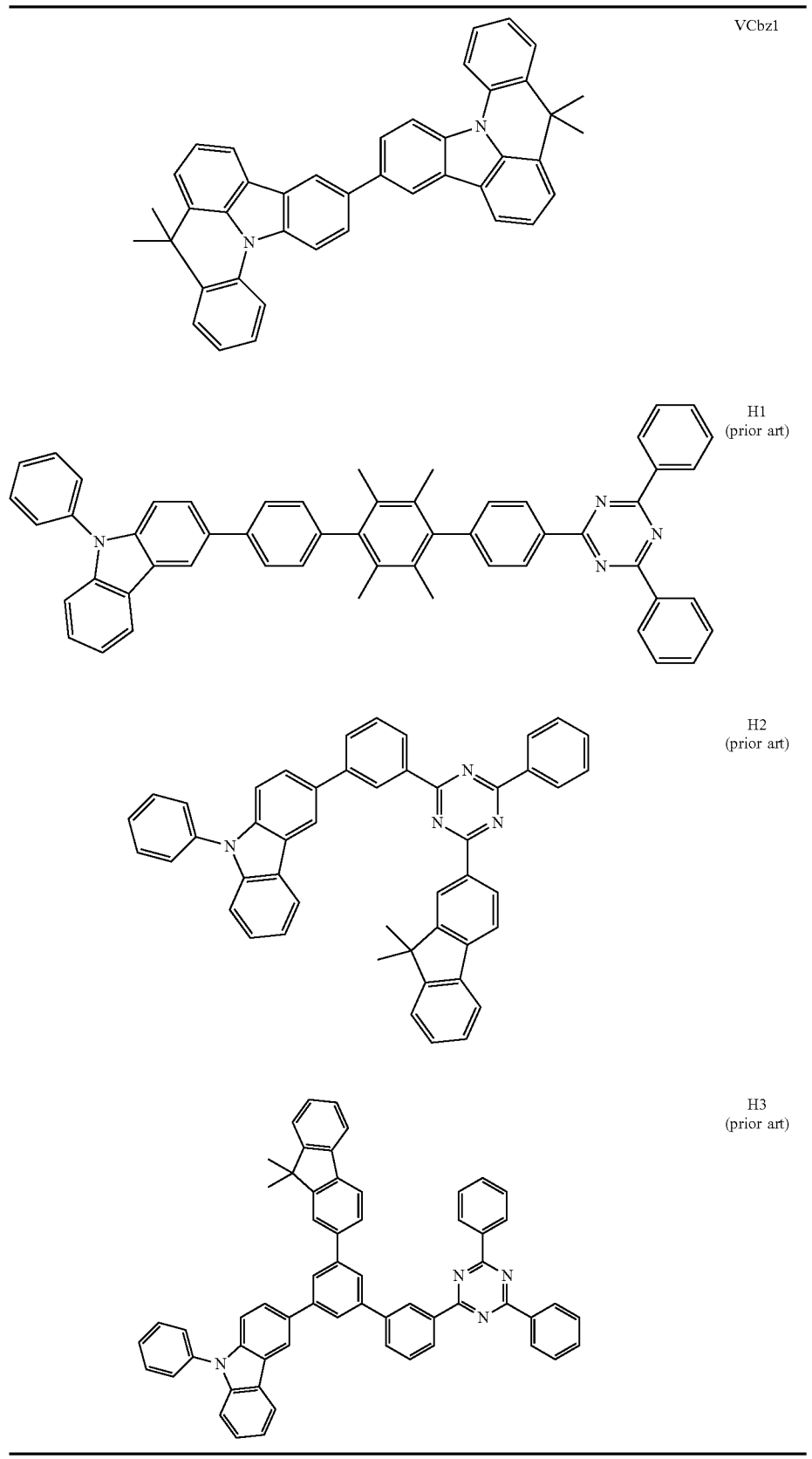
VCbz1
H1
(prior art)
H2
(prior art)
H3
(prior art)

The invention claimed is:
1. An organic electroluminescent device which comprises a compound of the formula (2a)

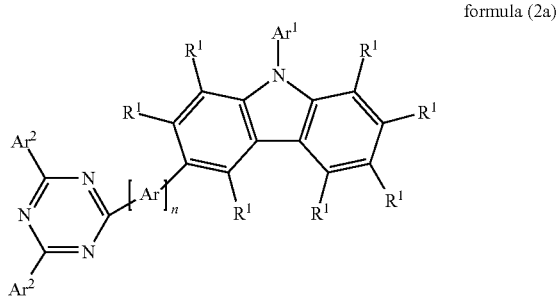

formula (2a)

where the following applies to the symbols and indices used:

Ar is on each occurrence, identically or differently, a phenylene group, which is optionally substituted by one or more radicals R; wherein the phenylene is identically or differently selected from the formulae (3), (4) or (5),

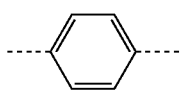

formula (3)

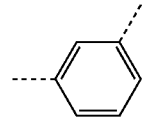

formula (4)

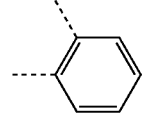

formula (5)

where the dashed bond in each case indicates the linking of these groups and each of these groups is optionally substituted by one or more radicals R and wherein at least one of the phenylene groups is a group of formula (4) or formula (5), $Ar^1$ is an aromatic ring system having 6 to 24 aromatic ring atoms which contains no condensed aryl groups having more than 10 aromatic ring atoms and which is optionally substituted by one or more radicals $R^1$, or is a dibenzofuran or dibenzothiophene group, each of which is optionally substituted by one or more radicals $R^1$;

$Ar^2$ is on each occurrence, identically or differently, an aryl group, where the aryl group has 6 to 10 aromatic ring atoms and is optionally substituted by one or more non-aromatic radicals $R^1$, or is a dibenzofuran or dibenzothiophene group, each of which is optionally substituted by one or more radicals $R^1$;

R is on each occurrence, identically or differently, H, D, F, CN, an aryl group, a biaryl group, a triaryl group or quateraryl group, where each individual aryl group in the above-mentioned groups has 6 to 10 aromatic ring atoms and is optionally substituted by one or more radicals $R^1$, or a carbazole group which is linked via a carbon atom and which may also be substituted by one or more radicals $R^1$;

$R^1$ is on each occurrence, identically or differently, H, D, F, CN, a straight-chain alkyl or alkoxy group having 1 to 20 C atoms or a branched or cyclic alkyl or alkoxy group having 3 to 20 C atoms, where one or more non-adjacent $CH_2$ groups is optionally replaced by $R^2C=CR^2$, $C≡C$ or O and where one or more H atoms is optionally replaced by D or F, or an aryl group having 6 to 10 C atoms, which is optionally substituted by one or more radicals $R^2$, or is a dibenzofuran or dibenzothiophene group, each of which is optionally substituted by one or more radicals $R^2$, or a carbazole group which is linked via a carbon atom and which may also be substituted by one or more radicals $R^2$, or an aralkyl group having 6 to 10 aromatic ring atoms, which is optionally substituted by one or more radicals $R^2$; two adjacent substituents $R^1$ here, together with the atoms to which they are bonded, may also form a mono- or polycyclic, aliphatic ring system with one another;

$R^2$ is on each occurrence, identically or differently, H, D or an aliphatic hydrocarbon radical having 1 to 20 C atoms or an aryl group having 6 to 10 ring atoms;

n is 2, 3 or 4, wherein the compound of the formula (2a) is employed as matrix material for phosphorescent emitters in an emitting layer.

2. The organic electroluminescent device according to claim 1, wherein the group —(Ar)$_n$— is selected from the formulae (9) to (18),

formula (10)

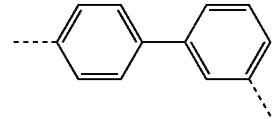

formula (11)

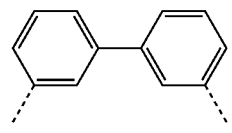

formula (12)

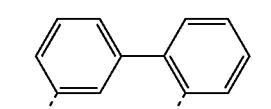

formula (13)

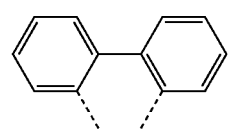

formula (14)

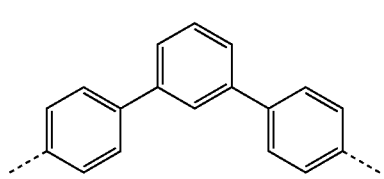

formula (16)

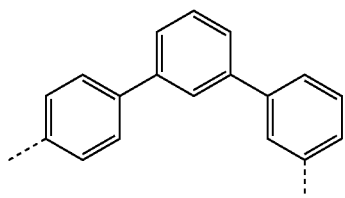
formula (17)

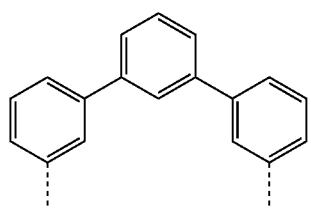
formula (18)

where the dashed bond in each case indicates the linking of these groups, each of these groups may also be substituted by one or more radicals R, and R and $R^1$ have the meanings given in claim 1.

3. The organic electroluminescent device according to claim 1, wherein the radical R is selected, identically or differently on each occurrence, from the group consisting of H, D, F, CN, phenyl, biphenyl or terphenyl, where each of the aryl groups in the above-mentioned groups is optionally substituted by one or more radicals $R^1$, and $R^1$ stands, identically or differently on each occurrence, for H or an alkyl group having 1 to 5 C atoms; or a carbazole group which is linked via a carbon atom and which is optionally substituted by one or more radicals $R^1$.

4. The organic electroluminescent device according to claim 1, wherein $Ar^1$ is selected from the group consisting of phenyl, biphenyl, terphenyl or quaterphenyl, each of which is optionally substituted by one or more radicals $R^1$.

5. The organic electroluminescent device according to claim 1, wherein $Ar^2$ is selected, identically on each occurrence, from the group consisting of phenyl which is optionally substituted by one or more non-aromatic radicals $R^1$.

6. The organic electroluminescent device according to claim 1, wherein the following applies to the symbols and indices:
n=2 or 3;
R is selected, identically or differently on each occurrence, from the group consisting of H, D, F, CN, phenyl, biphenyl or terphenyl, where each of the aryl groups is optionally substituted by one or more radicals $R^1$, and $R^1$ stands, identically or differently on each occurrence, for H or an alkyl group having 1 to 5 C atoms; or a carbazole group which is linked via a carbon atom and which may also be substituted by one or more radicals $R^1$;
$Ar^1$ is selected from the group consisting of phenyl, biphenyl, terphenyl or quaterphenyl, each of which is optionally substituted by one or more radicals $R^1$;
$Ar^2$ is selected, identically on each occurrence, from the group consisting of phenyl which is optionally substituted by one or more non-aromatic radicals $R^1$;
$R^1$ is selected on each occurrence, identically or differently, from the group consisting of H, D, F, a straight-chain alkyl group having 1 to 10 C atoms or a branched or cyclic alkyl group having 3 to 10 C atoms, where one or more non-adjacent $CH_2$ groups is optionally replaced by $R^2C=CR^2$ and where one or more H atoms is optionally replaced by F, or an aryl group having 6 to 10 C atoms, which is optionally substituted by one or more radicals $R^2$, or is a dibenzofuran or dibenzothiophene group, each of which is optionally substituted by one or more radicals $R^2$, or a carbazole group which is linked via a carbon atom and which may also be substituted by one or more radicals $R^2$.

7. The organic electroluminescent device according to claim 1, wherein Ar is on each occurrence, identically or differently, a phenylene group, which is optionally substituted by one or more radicals R.

8. The organic electroluminescent device according to claim 1, wherein n=2 or 3.

9. The organic electroluminescent device according to claim 1, wherein $Ar^2$ are identical.

* * * * *